US009133500B2

(12) United States Patent
Frisch et al.

(10) Patent No.: US 9,133,500 B2
(45) Date of Patent: Sep. 15, 2015

(54) SCREENING STRATEGIES FOR THE IDENTIFICATION OF BINDERS

(75) Inventors: Christian Frisch, München (DE);
Achim Knappik, Moorenweis (DE);
Alex Y. Strongin, San Diego, CA (US);
Sergey A. Shiryaev, San Diego, CA (US)

(73) Assignee: MorphoSys A6, Martinsried (DE)

( * ) Notice: Subject to any disclaimer, the term of this patent is extended or adjusted under 35 U.S.C. 154(b) by 19 days.

(21) Appl. No.: 13/379,680

(22) PCT Filed: Aug. 6, 2010

(86) PCT No.: PCT/EP2010/061522
§ 371 (c)(1),
(2), (4) Date: Mar. 8, 2012

(87) PCT Pub. No.: WO2011/018421
PCT Pub. Date: Feb. 17, 2011

(65) Prior Publication Data
US 2012/0178909 A1     Jul. 12, 2012

Related U.S. Application Data

(60) Provisional application No. 61/232,561, filed on Aug. 10, 2009, provisional application No. 61/233,504, filed on Aug. 13, 2009.

(51) Int. Cl.
| C12Q 1/70 | (2006.01) |
| C12Q 1/37 | (2006.01) |
| A61K 39/395 | (2006.01) |
| C07K 14/005 | (2006.01) |
| C07K 16/10 | (2006.01) |
| C07K 16/40 | (2006.01) |

(52) U.S. Cl.
CPC ............... *C12Q 1/37* (2013.01); *C07K 14/005* (2013.01); *C07K 16/1081* (2013.01); *C07K 16/40* (2013.01); *C07K 2299/00* (2013.01); *C07K 2317/21* (2013.01); *C07K 2317/33* (2013.01); *C07K 2317/515* (2013.01); *C07K 2317/55* (2013.01); *C07K 2317/565* (2013.01); *C07K 2317/76* (2013.01); *C07K 2317/92* (2013.01); *C12N 2770/24122* (2013.01); *G01N 2333/185* (2013.01); *G01N 2333/95* (2013.01); *G01N 2500/04* (2013.01)

(58) Field of Classification Search
CPC ............. C07K 16/1081; G01N 33/573; A61K 39/3955
See application file for complete search history.

(56) References Cited

U.S. PATENT DOCUMENTS

| 5,945,329 A * | 8/1999 | Breddam et al. ............... 435/223 |
| 7,572,456 B2 | 8/2009 | Johnson |
| 2009/0029924 A1* | 1/2009 | Strongin et al. ................ 514/15 |
| 2009/0258011 A1 | 10/2009 | Diamond |

FOREIGN PATENT DOCUMENTS

| WO | 2005010485 | 2/2005 |
| WO | 2006136601 | 12/2006 |

OTHER PUBLICATIONS

Nall et al., The Journal of Biological Chemistry, 2004, 179:48535-18542.*
Gao Junjun et al: "Two-state selection of conformation-specific antibodies." Proceedings of the national Academy of Sciences of the United States of America Mar. 3, 2009, vol. 106, No. 9.
Eckelman B P et al: "The mechanism of peptide-binding specificity of IAP BIR domains", Cell death and Differentiation, vol. 15, No. 5, May 2008.
Pereira Mark P et al: "High-throughput screening identifies novel inhibitors of the acetyltranfserase activity of *Escherichia coli* GlmU" Antimicobial Agents and Chemotherapy Jun. 2009.
Kasai N et al: "Inhibition of the hepatitis C virus NS3 protease activity by Fv fragment of antibody 8D4" Biochemical abd Biophysical Research Communications, Academic Press Inc. vol. 281, No. 2; Feb. 23, 2001.
Stoermer Martin J et al: "Potent cationic inhibitors of West Nile Virus NS2B/NS3 protease with serum stability, cell permeability and antiviral activity" Journal of Medicinal Chemistry, Vo. 51, No. 18, Sep. 2008.
Shiryaev Sergey A et al: "Isolation and characterization of selective and potent human Fab inhibitors directed to the active-site region of the two-component NS2B-NS3 proteinase of West Nile virus" Biochemical Journal. The Biochemical Society, London, GB, vol. 427, No. 3, May 1, 2010.
International Search Report from PCT/EP2010/061522.
Written Opinion from PCT/EP2010/061522.
Kim C-H et al: Effective selection of the monoclonal antibodies inhibiting the enzymatic activity of the bifunctional amylase-pullulanase produced by *Bacillus circulans*.

* cited by examiner

*Primary Examiner* — Stacy B Chen
(74) *Attorney, Agent, or Firm* — Paul F. Wiegel

(57) ABSTRACT

The present invention discloses novel screening strategies for the identification of binders that target the active site of enzymatic antigens. The present invention also discloses antigen-binding moieties which bind to the NS2B-NS3 Proteinase of West Nile Virus, in particular binders which bind to the active site, thereby inhibiting the enzymatic activity of the proteinase. The antigen-binding moieties of the present invention have numerous therapeutic and diagnostic applications.

9 Claims, 7 Drawing Sheets

Matriptase-E2

CARPVLTYPDRRGPQNVSP

NS2B-NS3pro-05323

Figure 2:
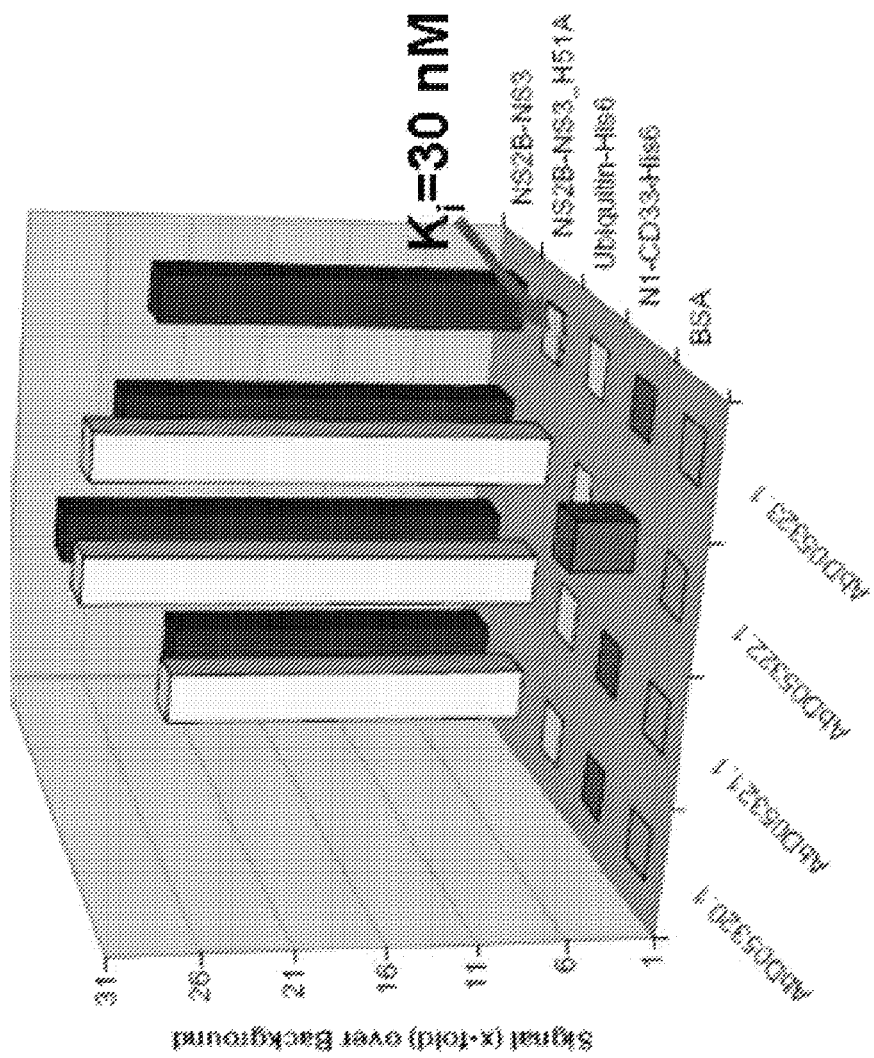

CARYNYKMGLNDAANTGG
CARYNYKMGRRGAANTGG

SCREENING STRATEGIES FOR THE IDENTIFICATION OF BINDERS

CROSS-REFERENCE TO RELATED APPLICATION

This application claims the benefit of U.S. provisional application Ser. No. 61/232,561 filed Aug. 10, 2009 and U.S. provisional application Ser. No. 61/233,504 filed Aug. 13, 2009, which are both incorporated by reference in their entireties.

GOVERNMENT INTEREST

This invention was made with government support under Grants AI061139, RR020843 and AI055789 awarded by the National Institutes of Health. The government has certain rights in the invention.

BACKGROUND OF THE INVENTION

The development and research of antigen binding moieties is a field which rapidly has processed within the last 30 years. Meanwhile particularly monoclonal antibodies are well established as biotherpeutic agents but also other scaffolds comprising target specificity already entered the market or proceed in development. Apart from that the use of antibodies and fragments thereof are self evident and indispensable for research purposes.

For the selection of antigen binding moieties a wide range of different techniques are in use. Apart of the isolation of antibody-producing hybridoma from immunized mammals the use of synthetic libraries for phage or yeast display are only few of many examples.

However, the selection process to isolate the target-specific candidates from a highly diverse library is a crucial step within any antibody generation project and therefor many different strategies and procedures are well established. Generally, the selection process comprises the incubation of the library with the antigen and the subsequent isolation of antibody-antigen complexes. Thereby the antigen can be presented to the library in solution, immobilized on a solid phase or presented on a cell. However in order to select antigen binding moieties which are directed to a specific epitope, domain or site of an antigen these strategies are limited and desired candidates are isolated only by chance and thus have to be identified during extensive experimental characterization.

However in certain cases a binding moiety which detects only a specific variant of an antigen or a specific relevant epitope is necessary. Thereby the specificity of the antibody shall be directed to for example specific isoforms or splice variants of antigens or only to monomeric or heteromeric compositions of the target. Furthermore the detection of an active form but not the inactive form of an enzyme states another scenario which necessitates an epitope or site-directed selection.

Antibodies targeting disease-relevant enzymes are not only relevant for research purposes but also for use as a therapeutic agent or diagnostic tool for many indications. For example the antagonism of proteases can be used to inhibit uncontrollable bleeding during surgery exemplified by the development of the trypsin inhibitor Aprotinin but also Kallikrein Inhibitors that were described to be potentially useful not only to reduce blood loss during surgery but also to treat allery mediated hereditary angioedema. Furthermore sectreted proteases from pathogens provide additional potential targets for therapeutic but also diagnostic antibodies.

A specific example is the NS2B-NS3 proteinase (NS2B-NS3pro) expressed by the West Nile virus (WNV) which is a virus of the family Flaviviridae. It mainly infects birds, but is known to infect humans, horses, dogs, cats, bats, chipmunks, skunks, squirrels, and domestic rabbits. The main route of human infection is through the bite of an infected mosquito. WNV may have different effects on humans—asymptomatic infection; a mild febrile syndrome termed West Nile Fever; or a neuroinvasive disease termed West Nile meningitis or encephalitis.

2007, in the United States 2007 there were a total of 3,630 cases of WNV neuroinvasive disease (WNND) and 124 deaths were reported (MMWR Morb. Mortal. Wkly. Rep. 57 (26): 720-3. July 2008). 3.4% of the serious infections of WNV were fatal.

WNV control is largely achieved through mosquito control, by elimination of mosquito breeding sites, larviciding active breeding areas and encouraging personal use of mosquito repellents. Along with such efforts go environmental concerns and questions whether the detrimental health effects of spraying pesticides outweigh the relatively few lives which may be saved.

There is no specific treatment for West Nile virus infection. Intensive supportive therapy is directed toward the complications of brain infections. Anti-inflammatory medications, intravenous fluids, and intensive medical monitoring may be required in severe cases. There is no specific antibiotic or antidote for the viral infection. There is also no vaccine to prevent the virus. Amongst the therapeutics under investigation is AMD 3100 (Plerixafor, Genzyme, Inc.), a small organic compound which has been proposed as an antiretroviral drug for HIV, and morpholino antisense oligonucleotides conjugated to cell penetrating peptides (AVI BioPharma, Inc.) There have also been attempts to treat infections using ribavirin, intravenous immunoglobulin, or alpha interferon, and it has been found that blocking angiotensin II can treat the "cytokine storm" induced by WNV (Curr Top Med Chem 4 (13): 1433-54). We are however still far from an effective therapy for this emerging virus.

WNV is an enveloped, positive-stranded, 11-kb RNA virus. The genomic RNA of WNV encodes a polyprotein precursor which consists of three structural proteins (C, capsid; prM, membrane, and E, envelope) and seven non-structural proteins (NS1, NS2A, NS2B, NS3, NS4A, NS4B and NS5) arranged in the order C-prM-E-NS1-NS2A-NS2BNS3-NS4A-NS4B-NS5.

Polyprotein processing by the viral two component NS2B-NS3 proteinase (NS2B-NS3pro) and also by the host cell secretase and furin is required to generate individual viral proteins. The full-length NS3 is a multifunctional protein in which the N-terminal 184 amino acid residues represent the NS3pro domain and the C-terminal sequence codes for the enzyme with the helicase, nucleoside triphosphatase and RNA triphosphatase activities, all of which are coordinately regulated through localization within membrane compartments in the infected cell. NS2B functions as an essential cofactor of NS3pro. The cofactor activity of the 48 amino acid central portion of NS2B is roughly equivalent to that of the entire NS2B sequence (Biochem J. 401, 743-752). Structural studies have determined that NS2B wraps around NS3pro, completing, in a precise and well-defined fashion, the structure of the active site. In agreement, deletion of the NS2B sequence inactivates the functional activity of NS3pro (J. Virol. 78, 13708-13716).

NS3pro is responsible for the cleavage of the capsid protein C and at the NS2A/NS2B, NS2B/NS3, NS3/NS4A, NS4A/NS4B and NS4B/NS5 boundaries. Because inactivating mutations of the NS3pro cleavage sites in the polyprotein precursor abolished viral infectivity (J. Virol. 67, 6797-6807; Curr Med. Chem. 15, 2771-2784) it is a reasonable expectation that the NS3pro function is vitally important for the virus, and that NS3pro antagonists have may have merit as viral drugs.

Several peptide and small organic inhibitors of NS3pro have recently been identified (PLoS Negl Trop Dis. 3, e356; Assay Drug Dev Technol. 5, 737-750; J Med. Chem. 49, 6585-6590; Antiviral Res. 80, 94-101; J Gen Virol. 88, 2223-2227; Antimicrob Agents Chemother. 52, 3385-3393; J Med. Chem. 51, 5714-5721; Antiviral Res. 82, 110-114). There are, however, obstacles which all of these molecules, e.g. inefficient cell penetration, poor solubility and lack of stability.

Antibodies could provide a much sought, excellent scaffold for designing inhibitors targeted to this enzyme. Over the past decade recombinant technology has enabled the production of engineered antibody fragments such as Fabs or single-chain FV (scFv) fragments and phage display technology has been used successfully for the isolation of specific scFv or Fab from human repertoire libraries (Curr. Opin. Biotechnol. 13, 598-602). For phage display selection, the Fab format is preferred since scFv fragments have a high tendency to form multimers. Fab are more stable compared to scFv fragments and tend to stay completely monomeric, allowing selection for affinity in contrast to selection for avidity.

In the present application we describe a novel screening strategy which enables the selection of antigen binding moieties that target only a specific epitope, site or domain of an antigen. To exemplify the effectiveness of the claimed selection strategy we describe the first successful generation of antibodies against WNV NS2B-NS3pro which are highly selective and target the active-site of WNV NS2B-NS3pro. Various uses and analysis upon application of the antibodies of the present invention are disclosed herein below. The generation of antibodies or antibody fragments which are directed only to the active variant of an enzyme enables the development of more efficient therapeutic agents. The specificity only for the variant which is therapeutically relevant facilitates the development of highly efficient antibodies with reduced side effects due to lacking cross-reactivity to the inactive form accompanied by the advantage that lower doses have to be administered. Additionally the disclosed screening method dismisses all antibodies targeting an irrelevant epitope and therby accelerates lead candidate identification and development. Furthermore the antibodies that bind specifically to the active site of a protein isolated by the disclosed screening method can be used for the identification of idiotypic antibodies which mimic the activity of the enzyme/protein. In turn such antibodies bearing enzymatic activity can be used for therapeutic purposes.

SUMMARY OF THE INVENTION

In certain embodiments the present invention discloses a method to identify antigen-binding moieties which bind to a selected site of an antigen, said method comprising
(a) screening a library of antigen-binding moieties against an antigen comprising the selected site and isolating those members of said library that bind to said antigen,
(b) counter-screening the members of the library isolated in step (a) against a variant of the antigen, wherein said variant antigen is devoid of the selected site, and
(c) isolating those members that do not bind to said variant antigen.

In certain embodiments of the present invention said selected site of the antigen is an epitope of the antigen.

In certain embodiments of the present invention said variant antigen is an epitope mutant of the wild type antigen.

In certain embodiments of the present invention said selected site of the antigen only exists within one or more isoforms of the antigen.

In certain embodiments of the present invention said selected site of the antigen only exists in the monomeric, multimeric or hereromeric form of the antigen.

In certain embodiments of the present invention said antigen has an enzymatic activity.

In certain embodiments of the present invention the variant antigen is used for counter-screening the members of a library isolated from a prior screening of a library of antigen-binding moieties against an antigen comprising the selected site, wherein said variant antigen is an epitope mutant of the wild type antigen.

In certain embodiments of the present invention said variant antigen is an epitope mutant of the wild type antigen.

In certain embodiments of the present invention the variant antigen is used for counter-screening the members of a library isolated from a prior screening of a library of antigen-binding moieties against an antigen comprising the selected site, wherein said variant antigen is an active site mutant of the wild type antigen.

In certain embodiments of the present invention said variant antigen is an active site mutant of the wild type antigen.

In certain embodiments of the present invention said antigen is a protease. In certain embodiments of the present invention said protease is a viral protease, such as NS2B-NS3 proteinase of West Nile Virus.

In certain embodiments the present invention discloses a method to identify antigen-binding moieties which bind to a selected site of an antigen, said method comprising
(a) screening a library of antigen-binding moieties against an antigen comprising the selected site and isolating those members of said library that bind to said antigen,
(b) counter-screening the members of the library isolated in step (a) against a variant of the antigen, wherein said variant antigen is devoid of the selected site,
(c) isolating those members that do not bind to said variant antigen, and
(d) testing if the antigen-binding moieties isolated in step (c) inhibit the enzymatic activity of the antigen.

In certain embodiments the present invention provides antigen-binding moieties identified according to the methods provided by the present invention.

In certain embodiments the present invention discloses the use of a first polypeptide comprising an enzymatic activity and a second polypeptide for the isolation of antigen-binding moieties that inhibit the enzymatic activity of the first polypeptide, wherein said second polypeptide is a variant of said first polypeptide which is devoid of enzymatic activity.

In certain embodiments the present invention discloses isolated antigen-binding moieties, or fragments thereof, which bind NS2B-NS3 proteinase of West Nile Virus.

In other embodiments the present invention discloses isolated antigen-binding moieties, or fragments thereof, which bind to the active site NS2B-NS3 proteinase of West Nile Virus.

In yet other embodiments the present invention discloses isolated antigen-binding moieties, or fragments thereof, which inhibit the enzymatic activity of NS2B-NS3 proteinase of West Nile Virus.

In certain embodiments the present invention discloses isolated antigen-binding moieties, or fragments thereof, which bind NS2B-NS3 proteinase of West Nile Virus, but which do not bind to active site mutants of NS2B-NS3 proteinase of West Nile Virus, such as a H51A, a T52V or a R76L mutant.

In certain embodiments the present invention discloses isolated antigen-binding moiety wherein said antigen-binding moiety comprises a H-CDR3 region selected from the group consisting of SEQ ID NOs: 4, 12, 20, 28, 36, 44, and 52.

In certain embodiments the present invention discloses isolated antigen-binding moieties comprising a H-CDR3 region selected from anyone of the H-CDR3 regions shown in Table 2. In certain embodiments the antigen-binding moieties further comprise a H-CDR1 region selected from anyone of the H-CDR1 regions shown in Table 2 and/or a H-CDR2 region selected from anyone of the H-CDR2 regions shown in Table 2. In further embodiments the antigen-binding moiety comprises a heavy chain variable region selected from anyone of the heavy chain variable (VH) regions shown in Table 2.

In certain embodiments the present invention discloses isolated antigen-binding moieties comprising a L-CDR1 region selected from anyone of the L-CDR1 regions shown in Table 2 and/or a L-CDR2 region selected from anyone of the L-CDR2 regions shown in Table 2 and/or a L-CDR3 region selected from anyone of the L-CDR3 regions shown in Table 2. In further embodiments the antigen-binding moiety comprises a light chain variable region selected from anyone of the light chain variable (VL) regions shown in Table 2. In certain embodiments the present invention discloses isolated antigen-binding moieties in which said antigen-binding moiety comprises a H-CDR3 region selected from the group consisting of SEQ ID NOs: 57-71.

In certain embodiments the present invention discloses isolated antigen-binding moieties in which said antigen-binding moiety comprises a H-CDR1 region selected from the group consisting of SEQ ID NOs: 2, 10, 18, 26, 34, 42, and 50, and/or a H-CDR2 region selected from the group consisting of SEQ ID NOs: 3, 11, 19, 27, 35, 43, and 51.

In certain embodiments the present invention discloses isolated antigen-binding moieties in which said antigen-binding moiety comprises a heavy chain variable region selected from the group consisting of SEQ ID NOs: 1, 9, 17, 25, 33, 41 and 49.

In certain embodiments the present invention discloses isolated antigen-binding moieties in which said antigen-binding moiety comprises a L-CDR1 region selected from the group consisting of SEQ ID NOs: 6, 14, 22, 30, 38, 46, and 54, and/or a L-CDR2 region selected from the group consisting of SEQ ID NOs: 7, 15, 23, 31, 39, 47, and 55, and/or a L-CDR3 region selected from the group consisting of SEQ ID NOs: 8, 16, 24, 32, 40, 48, and 56.

In certain embodiments the present invention discloses isolated antigen-binding moieties in which said antigen-binding moiety comprises a light chain variable region selected from the group consisting of SEQ ID NOs: 5, 13, 21, 29, 37, 45, and 53.

In certain embodiments the present invention discloses isolated antigen-binding moieties, wherein said antigen-binding moieties have an Ki of less than 300 nM, less than 200 nM, less than 100 nM, less than 75 nM or less than 50 nM against wild type NS2B-NS3 proteinase of West Nile Virus.

In other embodiments the present invention discloses isolated antigen-binding moieties, wherein the Ki of said antigen-binding moieties against wild type NS2B-NS3 proteinase of West Nile Virus is at least 3-fold, at least 5-fold, at least 10-fold or at least 20-fold lower than the Ki against a T52V mutant of NS2B-NS3 proteinase of West Nile Virus.

In other embodiments the present invention discloses isolated antigen-binding moieties, wherein the Ki of said antigen-binding moiety against wild type NS2B-NS3 proteinase of West Nile Virus is at least 3-fold, at least 5-fold, at least 10-fold or at least 20-fold lower than the Ki against a R76L mutant of NS2B-NS3 proteinase of West Nile Virus.

Also contemplated are antibodies or fragments thereof, comprising any of the antigen-binding moieties recited herein above. In certain embodiments said antibodies are of the type IgG. In other embodiments said antibody fragments are a scFv or a Fab.

In certain embodiments said antibodies or antibody fragments are conjugated antibodies or antibody fragments. In certain embodiments said moiety conjugated to said antibodies or antibody fragments is selected from a therapeutic moiety, such as a cytotoxin or a radioactive metal ion, a moiety that modifies or induces a certain biological response, or a moiety which triggers, enables or facilitates internalization of the antigen-binding moiety or antibody into a host cell infected with West Nile Virus. In certain embodiments said moiety conjugated to said antibodies or antibody fragments triggers, enables or facilitates internalization of the antibody or the antibody fragment into a host cell infected with West Nile Virus.

In certain embodiments the present invention discloses isolated antigen-binding moieties which compete for binding to an epitope with an antigen-binding moiety, an antibody, or an antibody fragment according of the present invention.

In certain embodiments the present invention discloses isolated nucleic acids encoding an antigen-binding moieties, antibodies or antibody fragments of the present invention.

In certain embodiments the present invention discloses vectors comprising nucleic acids encoding an antigen-binding moieties, antibodies or antibody fragments of the present invention.

In certain embodiments the present invention discloses host cells comprising a vectors comprising nucleic acids encoding an antigen-binding moieties, antibodies or antibody fragments of the present invention.

In certain embodiments the present invention discloses the use of an antigen-binding moiety, an antibody, or an antibody fragment of the present invention for the prophylaxis or treatment of an infection with West Nile Virus.

In certain embodiments the present invention discloses methods for preventing or treating an infection with West Nile Virus, said method comprising administering an antigen-binding moiety, an antibody, or an antibody fragment of the present invention to a patient infected or suspected to be infected with West Nile Virus.

In certain embodiments the present invention discloses the use of an antigen-binding moiety, an antibody, or an antibody fragment of the present invention for diagnosing or monitoring infection with West Nile Virus.

In certain embodiments the present invention discloses methods for diagnosing or monitoring an infection with West Nile Virus, said method comprising detecting West Nile Virus via an antigen-binding moiety, an antibody, or an antibody fragment of the present invention.

FIGURE LEGENDS

Figure 1:
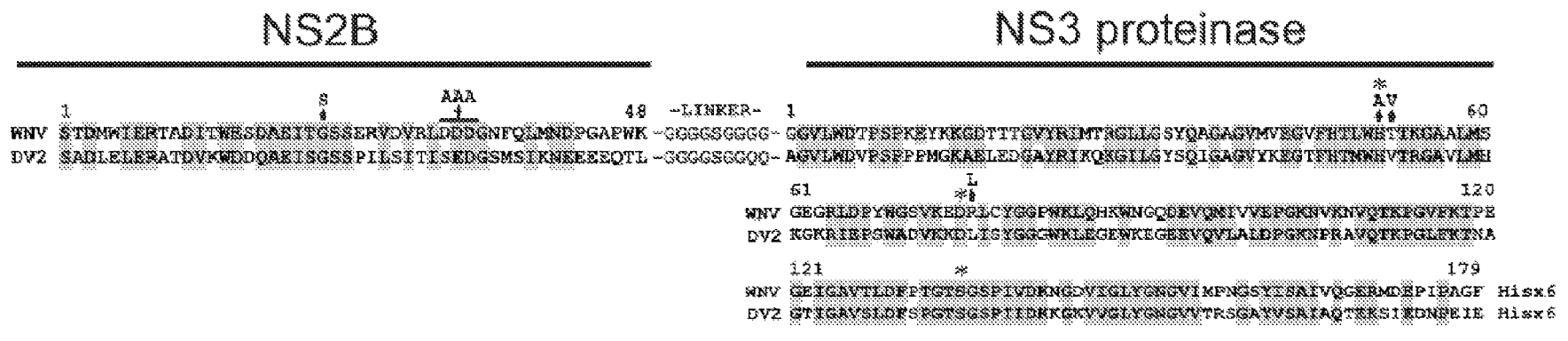

FIG. 1 shows a sequence alignment of the NS2B co-factor and the NS3 proteinase domain of the polypeptides from WNV strains NY99 and DV2, which are SEQ ID Nos. 72 and 73, respectively. Homologous amino acid residue positions are shaded. The stars above the sequences indicate His51, Asp75 and Ser135 of the catalytic triad. The arrows indicate mutations (G22S, DDD/AAA, H51A, T52V and R76L).

FIG. 2 indicates the binding of some isolated antibodies to certain constructs. The selection process of the antibodies was directed to the region proximal to the essential His51 of the catalytic triad. The purified wild-type NS2B-NS3 construct was used for screening of the phage antibody library while the inert H51A mutant (NS2B-NS3_H51A) with the mutation of the active site His51 was used for counter-screening. The constructs were C-terminally tagged with a Hisx6 tag. The antibodies, which recognize the wild-type enzyme and which do not recognize the mutant, were selected from the antibody library. BSA, ubiquitin-Hisx6 and CD33-Hisx6 were used as controls to eliminate the false-positive antibodies.

Figure 3:
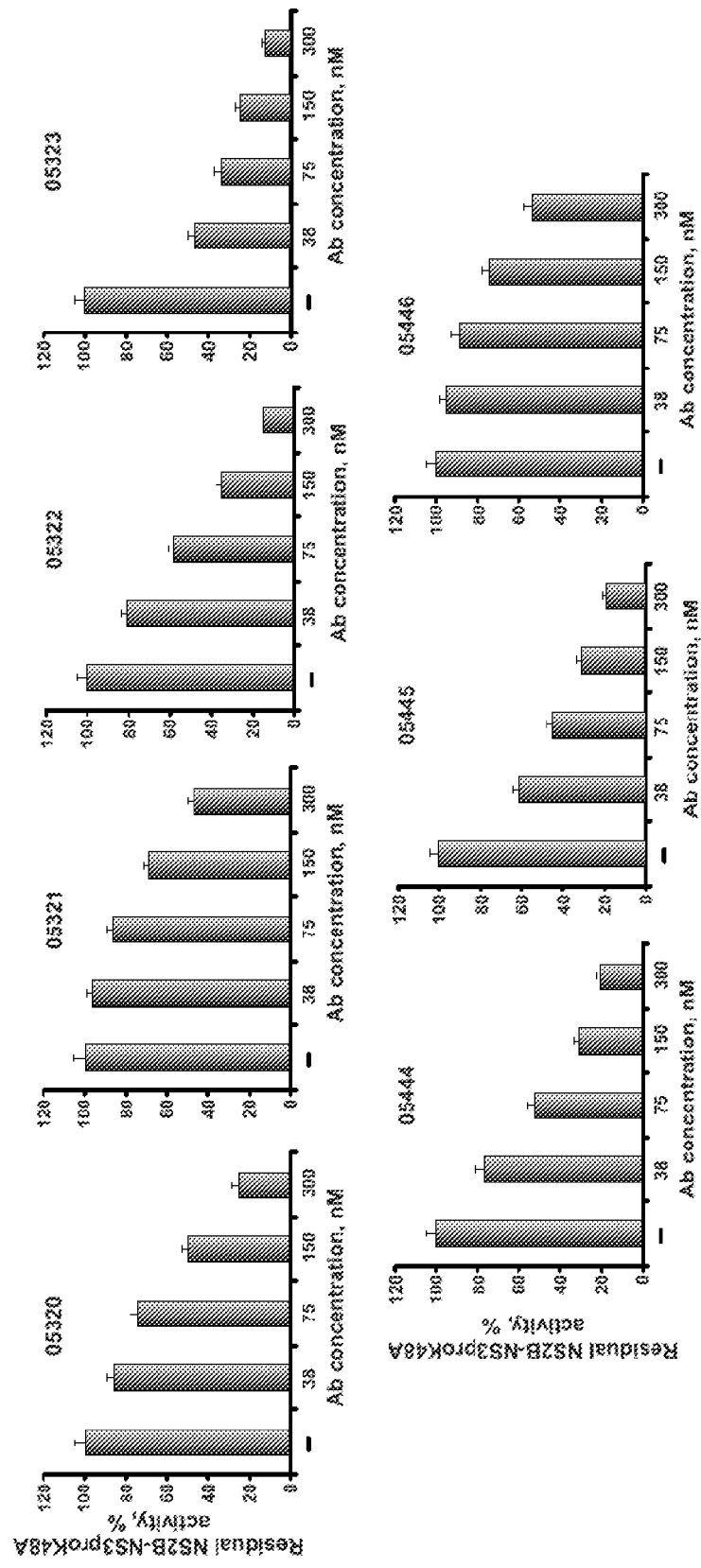

FIG. 3 shows the inhibition of the enzymatic activity of WNV NS2B-NS3pro by the antibodies of the present invention. Before the addition of the Pyr-RTKR-AMC substrate (25 mM), the purified WNV proteinase (50 nM) was co-incubated for 30 min with increasing concentrations of the antibodies. The residual activity was then monitored continuously at $\lambda_{ex}$=360 nm and $\lambda_{em}$=465 nm to determine the initial velocity of the reactions. The untreated proteinase was used as a control and its activity was counted as 100%.

FIG. 4 shows the results of the experiments used to determine the Ki values of the inhibitory antibodies. Before the addition of the Pyr-RTKR-AMC substrate (25 mM), the purified NY99 proteinase (10 nM) was co-incubated for 30 min with increasing concentrations of the antibodies. The cleavage of the Pyr-RTKR-AMC peptide by the proteinase was monitored to determine the Ki values.

FIG. 5 shows a Western Blot. Various NS2B-NS3 mutants (indicated on the top of the graph) were probed with various antibodies of the present invention. The purified mutant constructs were analysed by SDS-gel electrophoresis (4 μg/lane) followed by Coomassie staining (CS) and by Western blotting (100 ng/lanes) with a His-tag antibody and the selected AbD05320, AbD05321, AbD05322, AbD05323, AbD05444, AbD05445 and AbD05446 antibodies (indicated on the right). The H51A, T52V and R76L WNV NS2B-NS3 mutants do not interact with the AbD05323 and AbD05444 antibodies. Note that AbD05323 and AbD05444 did not bind with the H51A, T52V and R76L constructs which exhibit mutations in the active site proximity.

FIG. 6 shows a ELISA of the NS2B-NS3pro constructs. The antibodies were allowed to interact with the native wild-type (WT) and mutant NY99 constructs and with the wild-type DV2 constructs. The binding efficiency is expressed as α-fold increase relative to control (BSA).

FIG. 7 shows the proposed re-design of the AbD05323 antibody sequence. The solid surface structure of E2-matriptase is shown on the left, and that of AbD05323-WNV NS2B-NS3pro on the right. The antibody is shown in the lower parts of the panels (blue-light blue); the proteinase on the upper part (red). The close-up shows the E2 hypervariable loop in the matriptase active site (left), the original (right, top) and the re-designed AbD05323 hypervariable loop (right, bottom) in the NS3pro active site. The arrow indicates the proposed re-design of AbD05323. The catalytic triad is shown as sticks. Leu-Asn-Asp (right, top) and Arg-Arg-Gly (right, bottom) are shown as blue sticks. The antibody amino acid sequence 99-116 is shown at the bottom of the panels (the critical 108-110 residues are in bold), which are SEQ ID Nos. 74, 75 and 76, in order of appearance.

DETAILED DESCRIPTION OF THE INVENTION

Unless defined otherwise, all technical and scientific terms used herein have the same meaning as commonly understood by those of ordinary skill in the art to which this invention pertains.

In certain aspects the present invention provides a novel screening and identification method for antigen-binding moieties with novel and advantageous properties. Said method can be used to isolate antigen-binding moieties, for example antibodies, which bind to a selected site of an antigen. Thereby the selected site of an antigen is only present or displayed within a specific variant of the antigen. Thereby this specific variant can be a specific epitope of an antigen an active form of a protein or an isoform of a target family or a monomeric or heteromeric variant of an antigen but is not limited to that.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

With reference to the present invention an epitope preferably represents a specific site of an antigen which has functional relevance by either mediting activation or inhibition of a specific downstream processing and thereby defines a potential target site for a therapeutic or diagnostic agent. In this line epitope mutants represent variants of the antigen in which the relevant epitope is either removed or substituted by other amino acid. According to the selection method disclosed herein epitope mutant can be used for counterscreening to identify antigen binding moieties which are specific for the selected epitope of the antigen.

The terms "cross-block", "cross-blocked" and "cross-blocking" are used interchangeably herein to mean the ability of an antibody or other binding agent to interfere with the binding of other antibodies or binding agents to a certain epitope in a standard competitive binding assay. The ability or extent to which an antibody or other binding agent is able to interfere with the binding of another antibody or binding molecule to an epitope, and therefore whether it can be said to cross-block according to the invention, can be determined using standard competition binding assays. One suitable assay involves the use of the Biacore technology (e.g. by using the BIAcore 3000 instrument (Biacore, Uppsala, Sweden)), which can measure the extent of interactions using surface plasmon resonance technology. Another assay for measuring cross-blocking uses an ELISA-based approach. Such antibodies are also referred to as antibodies which "compete for binding" to an epitope.

Therefore, in certain embodiments, the present invention provides antigen-binding moieties which cross-block antigen-binding moieties, antibodies or antibody fragments specifically disclosed in the present invention.

Preferable, said antigen contains at least one enzymatic activity, such as protease activity. In particular aspects of the present invention, the novel screening method provides for the isolation of antigen-binding moieties which inhibit the enzymatic activity of the antigen. Enzymatic activities that may be targeted by the antigen-binding moieties isolated in accordance with the method of the present invention include oxidoreductase activity (oxidoreductases catalyze the transfer of electrons from one molecule to another), transferase activity (transferases catalyze the transfer of a functional group, e.g. a methyl or phosphate group, from one molecule to another), hydrolase activity (hydrolases catalyze the hydrolysis of a chemical bond), lyase activity (lyases catalyze the breaking of chemical bonds by means other than hydrolysis and oxidation), isomerase activity (isomerases catalyze the structural rearrangement of isomers) and ligase activity (ligases catalyse the joining of two molecules by forming a new chemical bond).

In certain aspects of the present invention the antigen-binding moieties isolated by the screening method are isolated form a library of antigen-binding moieties. Such library may be any kind of library, such as an antibody library, a Fab library, a scFv library or a phage display library. Such library may comprise more than $10^3$, more than $10^4$, more than $10^5$, more than $10^6$, more than $10^7$, more than $10^8$, more than $10^9$, more than $10^{10}$, more than $10^{11}$ or more than $10^{12}$ members.

In essence, an "active" antigen is used in an initial screening step to isolate members form a library of antigen-binding moieties that bind to said "active" antigen. The antigen is "active" in a sense that it comprises an activity or a functional property that differentiates it from a corresponding "inactive" variant of the same antigen. Such "inactive" variant is used in a second counter-screening step, in which those antigen-binding moieties are isolated which do not bind to said variant antigen. An "active" antigen may be an antigen that possesses an enzymatic activity and an "inactive" antigen a respective antigen which is devoid of the respective activity, e.g. due a mutation in the active site. An "active" antigen may also be an antigen which elicits an immune response and a corresponding "inactive" antigen an antigen which does not elicit an immune response. Other pairs of active and inactive antigens may however be used as well and will be self evident to the skilled artisan.

The term "isoform" refers to a different version of a protein that may be produced by different genes or from the same gene by alternative splicing as defined by the Unified Medical Language System at the National Library of Medicine. In certain embodiments isoforms may have the same function, and in alternate embodiments protein isoforms may have different functions.

With reference to the present invention an isoform preferably represents a specific variant of an antigen which is implicated to play a role in the induction and/or progression of specific diseases and thereby represents a reasonable target molecule for a therapeutic agent or a potential marker to be targeted by diagnostic agents.

As used herein the term "multimeric" generally refers to the aggregation state of an antigen wherein at least two species of the same antigen interact. Thus, the terms "heteromer" as used herein, refer to the state of at least two different species polypeptides associated with each other. And, the term "monomer" refers to a single peptide chain of an antigen.

With reference to the present invention a "multimeric" state of an antigen represents a reasonable diagnostic marker or therapeutic target if solely the occurrence of a specific aggregation state or its level of occurrence is in conjunction to the induction and/or progression of specific diseases.

In certain aspects the present invention provides for the use of a first polypeptide comprising an enzymatic activity and a second polypeptide for the isolation of antigen-binding moieties that inhibit the enzymatic activity of the first polypeptide, wherein said second polypeptide is a variant of said first polypeptide which is devoid of enzymatic activity.

The term "antigen binding moiety", as used herein, refers to one or more fragments that confer to a molecule the ability to specifically bind to a given antigen (e.g. NS2B-NS3 proteinase of West Nile Virus). Antibodies for example are molecules comprising antigen binding moieties. Antibody derivatives, antibody-like scaffolds and alternative scaffolds may do so as well. Examples of molecules comprising antigen binding moieties are given herein below and include fibronectin (Compound Therapeutics, Inc., Waltham, Mass.), camelid antibodies, ankyrin (Molecular Partners AG, Zurich, Switzerland), domain antibodies (Domantis, Ltd., Cambridge, Mass., and Ablynx nv, Zwijnaarde, Belgium), lipocalin (Pieris Proteolab AG, Freising, Germany), small modular immuno-pharmaceuticals (Trubion Pharmaceuticals Inc., Seattle, Wash.), maxybodies (Avidia, Inc., Mountain View, Calif.), Protein A (Affibody AG, Sweden), and affilin (gamma-crystallin or ubiquitin) (Scil Proteins GmbH, Halle, Germany).

The term "antibody" as used herein includes whole antibodies and any fragment or single chains thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementary determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. Antigen binding functions of an antibody can be performed by fragments of an intact antibody. Examples of binding fragments encompassed within the term "antibody fragment" of an antibody include a Fab fragment, a monovalent fragment consisting of the VL, VH, CL and CH1 domains; a F(ab)2 fragment, a bivalent fragment comprising two Fab fragments linked by a disulfide bridge at the hinge region; an Fd fragment consisting of the VH and CH1 domains; an Fv fragment consisting of the VL and VH domains of a single arm of an antibody; a single domain antibody (dAb) fragment (Ward et al., 1989 Nature 341:544-546), which consists of a VH domain; and an isolated complementary determining region (CDR).

The terms "heavy chain variable region CDR1" and "H-CDR1" are used interchangeably, as are the terms "heavy chain variable region CDR2" and "H-CDR2", the terms "heavy chain variable region CDR3" and "H-CDR3", the terms "light chain variable region CDR1" and "L-CDR1"; the terms "light chain variable region CDR2" and "L-CDR2" and the terms "light chain variable region CDR3" and "L-CDR3".

Furthermore, although the two domains of the Fv fragment, VL and VH, are coded for by separate genes, they can be joined, using recombinant methods, by an artificial peptide linker that enables them to be made as a single protein chain in which the VL and VH regions pair to form monovalent molecules (known as single chain Fv (scFv); see, e.g., Bird et al., 1988 Science 242:423-426; and Huston et al., 1988 Proc. Natl. Acad. Sci. 85:5879-5883). Such single chain antibodies include one or more antigen binding moieties. These antibody fragments are obtained using conventional techniques known to those of skill in the art, and the fragments are screened for utility in the same manner as are intact antibodies.

Antigen binding moieties can also be incorporated into single domain antibodies, maxibodies, minibodies, intrabodies, diabodies, triabodies, tetrabodies, v-NAR and bis-scFv (see, e.g., Hollinger and Hudson, 2005, Nature Biotechnology, 23, 9, 1126-1136). Antigen binding moieties of antibodies can be grafted into scaffolds based on polypeptides such as Fibronectin type III (Fn3) (see U.S. Pat. No. 6,703,199, which describes fibronectin polypeptide monobodies).

Antigen binding moieties can be incorporated into single chain molecules comprising a pair of tandem Fv segments (VH-CH1-VH-CH1) which, together with complementary light chain polypeptides, form a pair of antigen binding regions (Zapata et al., 1995 Protein Eng. 8(10):1057-1062; and U.S. Pat. No. 5,641,870).

Other antibody/immunoglobulin frameworks or scaffolds comprising "antigen-binding moieties" can be employed in line with the present invention. This includes non-immunoglobulin based antibodies and scaffolds onto which CDRs of the invention can be grafted.

The fibronectin scaffolds are based on fibronectin type III domain (e.g., the tenth module of the fibronectin type III (10 Fn3 domain)). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (see U.S. Pat. No. 6,818,418). These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen binding properties that are similar in nature and affinity to those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs of the invention using standard cloning techniques.

Camelid antibody proteins obtained from members of the camel and dromedary (Camelus bactrianus and Calelus dromaderius) family including new world members such as llama species (Lama paccos, Lama glama and Lama vicugna) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See WO 94/04678.

The ankyrin technology is based on using proteins with ankyrin derived repeat modules as scaffolds for bearing variable regions which can be used for binding to different targets. The ankyrin repeat module is a 33 amino acid polypeptide consisting of two anti-parallel α-helices and a β-turn. Binding of the variable regions is mostly optimized by using ribosome display.

Avimers are derived from natural A-domain containing protein such as LRP-1. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, U.S. Patent Application Publication Nos. 20040175756; 20050053973; 20050048512; and 20060008844.

Affibody affinity ligands are small, simple proteins composed of a three-helix bundle based on the scaffold of one of the IgG-binding domains of Protein A. Protein A is a surface protein from the bacterium Staphylococcus aureus. This scaffold domain consists of 58 amino acids, 13 of which are randomized to generate affibody libraries with a large number of ligand variants (See e.g., U.S. Pat. No. 5,831,012). Affibody molecules mimic antibodies, they have a molecular weight of 6 kDa, compared to the molecular weight of antibodies, which is 150 kDa. In spite of its small size, the binding site of affibody molecules is similar to that of an antibody.

Anticalins are products developed by the company Pieris ProteoLab AG. They are derived from lipocalins, a widespread group of small and robust proteins that are usually involved in the physiological transport or storage of chemically sensitive or insoluble compounds. Several natural lipocalins occur in human tissues or body liquids. The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain. The set of four loops, which makes up the binding pocket, shows pronounced structural plasticity and tolerates a variety of side chains. The binding site can thus be reshaped in a proprietary process in order to recognize prescribed target molecules of different shape with high affinity and specificity. One protein of lipocalin family, the bilin-binding protein (BBP) of Pieris Brassicae has been used to develop anticalins by mutagenizing the set of four loops. One example of a patent application describing anticalins is in PCT Publication No. WO 199916873.

Affilin molecules are small non-immunoglobulin proteins which are designed for specific affinities towards proteins and small molecules. New affilin molecules can be very quickly selected from two libraries, each of which is based on a different human derived scaffold protein. Affilin molecules do not show any structural homology to immunoglobulin proteins. Currently, two affilin scaffolds are employed, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of gamma crystalline derived proteins are described in WO200104144 and examples of "ubiquitin-like" proteins are described in WO2004106368.

Protein epitope mimetics (PEM) are medium-sized, cyclic, peptide-like molecules (MW 1-2 kDa) mimicking beta-hairpin secondary structures of proteins, the major secondary structure involved in protein-protein interactions.

The term "human antibody", as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences. The human antibodies of the invention may include amino acid residues not encoded by human sequences (e.g., mutations introduced by random or site-specific mutagenesis in vitro or by somatic mutation in vivo). Compared to the chimeric or humanized antibodies, antibodies of the invention have further reduced antigenicity when administered to human subjects.

As used herein, a human antibody comprises heavy or light chain variable regions or full length heavy or light chains that are "the product of" or "derived from" a particular germline sequence if the variable regions or full length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally occurring somatic mutations or intentional introduction of site-directed mutations. However, in the VH or VL framework regions, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene. Typically, a recombinant human antibody will display no more than 10 amino acid differences from the amino acid sequence encoded by the human germline immunoglobulin gene in the VH or VL framework regions. In certain cases, the human antibody may display no more than 5, or even no more than 4, 3, 2, or 1 amino acid difference from the amino acid sequence encoded by the germline immunoglobulin gene.

The terms "monoclonal antibody" as used herein refer to a preparation of antibody molecules of single molecular composition. A monoclonal antibody composition displays a single binding specificity and affinity for a particular epitope.

The term "human monoclonal antibody" refers to antibodies displaying a single binding specificity which have variable regions in which both the framework and CDR regions are derived from human sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

A "humanized" antibody is an antibody that retains the reactivity of a non-human antibody while being less immunogenic in humans. This can be achieved, for instance, by retaining the non-human CDR regions and replacing the remaining parts of the antibody with their human counterparts (i.e., the constant region as well as the framework portions of the variable region). See, e.g., Morrison et al., Proc. Natl. Acad. Sci. USA, 81:6851-6855, 1984; Morrison and Oi, Adv. Immunol., 44:65-92, 1988; Verhoeyen et al., Science, 239:1534-1536, 1988; Padlan, Molec. Immun., 28:489-498, 1991; and Padlan, Molec. Immun., 31:169-217, 1994. Other examples of human engineering technology include, but is not limited to Xoma technology disclosed in U.S. Pat. No. 5,766,886.

The term "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. For example, a mouse antibody can be modified by replacing its constant region with the constant region from a human immunoglobulin. Due to the replacement with a human constant region, the chimeric antibody can retain its specificity in recognizing the antigen while having reduced antigenicity in human as compared to the original mouse antibody.

In certain embodiments of the present invention the antigen-binding moieties, antibodies or fragments thereof, are human, humanized, chimeric or murine. In specific embodiments the antigen-binding moieties, antibodies or fragments thereof, are human or humanized. In other specific embodiments the antigen-binding moieties, antibodies or fragments thereof, are human.

The term "isolated antibody" refers to an antibody that is substantially free of other antibodies having different antigenic specificities. Moreover, an isolated antibody may be substantially free of other cellular material and/or chemicals.

The term "isotype" refers to the antibody class (e.g., IgM, IgE, IgG such as IgG1 or IgG4) that is provided by the heavy chain constant region genes. Isotype also includes modified versions of one of these classes, where modifications have been made to alter the Fc function, for example, to enhance or reduce effector functions or binding to Fc receptors.

In certain embodiments of the present invention the antigen-binding moieties of are of the type IgG, IgM, IgA, IGE or IgD. In specific embodiments the antigen-binding moieties of are of the type IgG.

In certain embodiments of the present invention the antigen-binding moieties of are of the subtype IgG1, IgG2, IgG3 or IgG4. In specific embodiments the antigen-binding moieties are of the subtype IgG1 or IgG4. In other specific embodiments the antigen-binding moieties are of the subtype IgG1.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., Nucleic Acid Res. 19:5081, 1991; Ohtsuka et al., J. Biol. Chem. 260:2605-2608, 1985; and Rossolini et al., Mol. Cell. Probes 8:91-98, 1994).

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

As used herein, the term, "optimized" means that a nucleotide sequence has been altered to encode an amino acid sequence using codons that are preferred in the production cell or organism, generally a eukaryotic cell, for example, a cell of Pichia, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence. The optimized sequences herein have been engineered to have codons that are preferred in mammalian cells. However, optimized expression of these sequences in other eukaryotic cells or prokaryotic cells is also envisioned herein. The amino acid sequences encoded by optimized nucleotide sequences are also referred to as optimized.

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "vector" is intended to refer to a polynucleotide molecule capable of transporting another polynucleotide to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

In certain embodiments the present invention provides nucleic acids encoding the antigen-binding moieties, the antibodies or the antibody fragments disclosed in the present invention. In certain embodiments there nucleic acids are isolated nucleic acids. In certain embodiments there nucleic acids are substantially purified nucleic acids.

In certain embodiments the present invention provides nucleic acids encoding the heavy chain variable region shown in SEQ ID NOs: 1, 9, 17, 25, 33, 41 and 49, and/or the nucleotide sequence encoding the light chain variable region shown in SEQ ID NOs: 5, 13, 21, 29, 37, 45, and 53. In a specific embodiment, the nucleic acid molecules are those encoding anyone of the variable regions or CDR regions shown in Table 2. Some other nucleic acid molecules of the invention comprise nucleotide sequences that are substantially identical (e.g., at least 65, 80%, 95%, or 99%) to the nucleotide sequences of those encoding the heavy chain variable region shown in SEQ ID NOs: 1, 9, 17, 25, 33, 41 and 49, and/or the nucleotide sequence encoding the light chain variable region shown in SEQ ID NOs: 5, 13, 21, 29, 37, 45, and 53. When expressed from appropriate expression vectors, polypeptides encoded by these polynucleotides are capable of exhibiting NS2B-NS3 proteinase-binding capacity.

Also provided in the present invention are polynucleotides which encode at least one CDR region and usually all three CDR regions from the heavy or light chain of the NS2B-NS3 proteinase-binding antigen-binding moieties set forth above. Some other polynucleotides encode all or substantially all of the variable region sequence of the heavy chain and/or the light chain of the NS2B-NS3 proteinase-binding antigen-binding moieties set forth above. Because of the degeneracy of the code, a variety of nucleic acid sequences will encode each of the immunoglobulin amino acid sequences.

The polynucleotide sequences can be produced by de novo solid-phase DNA synthesis or by PCR mutagenesis of an existing sequence (e.g., sequences as described in the Examples below) encoding an NS2B-NS3 proteinase-binding antigen-binding moiety. Direct chemical synthesis of nucleic acids can be accomplished by methods known in the art, such as the phosphotriester method of Narang et al., 1979, Meth. Enzymol. 68:90; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, N.Y., 1992; PCR Protocols: A Guide to Methods and Applications, Innis et al. (Ed.), Academic Press, San Diego, Calif., 1990; Mattila et al., Nucleic Acids Res. 19:967, 1991; and Eckert et al., PCR Methods and Applications 1:17, 1991.

The present invention also provides vectors, such as expression vectors comprising the nucleic acids of the present invention. Various expression vectors can be employed to express the polynucleotides encoding the NS2B-NS3 proteinase-binding antigen-binding moieties. Both viral-based and non-viral expression vectors can be used to produce the antibodies in a mammalian host cell. Non-viral vectors and systems include plasmids, episomal vectors, typically with an expression cassette for expressing a protein or RNA, and human artificial chromosomes (see, e.g., Harrington et al., Nat Genet. 15:345, 1997). For example, non-viral vectors useful for expression of the NS2B-NS3 proteinase-binding polynucleotides and polypeptides in mammalian (e.g., human) cells include pThioHis A, B & C, pcDNA3.1/His, pEBVHis A, B & C, (Invitrogen, San Diego, Calif.), MPSV vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding a NS2B-NS3 proteinase-binding antibody chain or fragment. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under non-inducing conditions without biasing the population for coding sequences whose expression products are better tolerated by the host cells. In addition to promoters, other regulatory elements may also be required or desired for efficient expression of an NS2B-NS3 proteinase-binding antibody chain or fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted NS2B-NS3 proteinase-binding antibody sequences. More often, the inserted NS2B-NS3 proteinase-binding sequences are linked to a signal sequences before inclusion in the vector. Vectors to be used to receive sequences encoding NS2B-NS3 proteinase-binding light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

Also provided in the present invention are host cells comprising a nucleic acid molecule or a vector as set forth in the present invention. In certain embodiments said host cell is a recombinant host cell.

The host cells for harboring and expressing the NS2B-NS3 proteinase-binding antigen-binding moiety can be either prokaryotic or eukaryotic. E. coli is one prokaryotic host useful for cloning and expressing the polynucleotides of the present invention. Other microbial hosts suitable for use include bacilli, such as *Bacillus subtilis*, and ther enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express NS2B-NS3 proteinase-binding antigen-binding moieties of the invention. Insect cells in combination with baculovirus vectors can also be used.

In some preferred embodiments, mammalian host cells are used to express and produce the NS2B-NS3 proteinase-binding antigen-binding moieties of the present invention. For example, they can be either a hybridoma cell line expressing endogenous immunoglobulin genes or a mammalian cell line harboring an exogenous expression vector. These include any normal mortal or normal or abnormal immortal animal or human cell. For example, a number of suitable host cell lines capable of secreting intact immunoglobulins have been developed including the CHO cell lines, various Cos cell lines, HeLa cells, myeloma cell lines, transformed B-cells and hybridomas. The use of mammalian tissue cell culture to express polypeptides is discussed generally in, e.g., Winnacker, FROM GENES TO CLONES, VCH Publishers, N.Y., N.Y., 1987. Expression vectors for mammalian host cells can include expression control sequences, such as an origin of replication, a promoter, and an enhancer (see, e.g., Queen, et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts. (See generally Sambrook, et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express NS2B-NS3 proteinase-binding antigen-binding moieties can be prepared using expression vectors of the invention which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

In certain embodiment, the present invention provides antigen-binding moieties comprising amino acid sequences that are homologous to the sequences shown in Table 2, wherein said antigen-binding moieties specifically bind to NS2B-NS3 proteinase of West Nile Virus, and retain the desired functional properties of the antigen-binding moieties of the present invention.

For example, the invention provides an isolated antigen-binding moieties or isolated monoclonal antibodies (or a functional antigen binding fragment thereof) comprising a heavy chain variable region and a light chain variable region, wherein the heavy chain variable region comprises an amino acid sequence that is at least 80%, at least 90%, or at least 95% identical to an amino acid sequence selected from the group consisting of SEQ ID NOs: 1, 9, 17, 25, 33, 41 and 49; the light chain variable region comprises an amino acid sequence that is at least 80%, at least 90%, or at least 95% identical to an amino acid sequence selected from the group consisting of SEQ ID NOs: 5, 13, 21, 29, 37, 45, and 53; and isolated antigen-binding moiety or isolated monoclonal antibody specifically binds to NS2B-NS3 proteinase of West Nile Virus.

In other embodiments, the VH and/or VL amino acid sequences may be 50%, 60%, 70%, 80%, 90%, 95%, 96%, 97%, 98% or 99% identical to the sequences set forth in anyone of the VH and/or VL amino acid sequences shown in Table 2. In other embodiments, the VH and/or VL amino acid sequences may be identical except an amino acid substitution in no more than 1, 2, 3, 4 or 5 amino acid position. An antigen-binding moiety or antibody having VH and VL regions having high (i.e., 80% or greater) identity to the VH and VL regions of those shown in Table 2 can be obtained by mutagenesis (e.g., site-directed or PCR-mediated mutagenesis) of nucleic acid molecules encoding the amino acid sequences of the VH and VL regions shown in Table 2, followed by testing of the encoded altered antibody for retained function using the functional assays described herein.

In other embodiments, the full length heavy chain and/or full length light chain amino acid sequences may be 50% 60%, 70%, 80%, 90%, 95%, 96%, 97%, 98% or 99% identical to the sequences set forth in anyone of the VH and/or VL amino acid sequences shown in Table 2. An antibody having a full length heavy chain and full length light chain having high (i.e., 80% or greater) identity to the full length heavy chains of any of SEQ ID NOs: 1, 9, 17, 25, 33, 41 and 49, and full length light chains of any of SEQ ID NOs 5, 13, 21, 29, 37, 45, and 53, respectively, can be obtained by mutagenesis (e.g., site-directed or PCR-mediated mutagenesis) of nucleic acid molecules encoding such polypeptides respectively, followed by testing of the encoded altered antibody for retained function using the functional assays described herein.

In other embodiments, the full length heavy chain and/or full length light chain nucleotide sequences may be 60%, 70%, 80%, 90%, 95%, 96%, 97%, 98% or 99% identical to the sequences set forth above.

In other embodiments, the variable regions of heavy chain and/or light chain nucleotide sequences may be 60%, 70%, 80%, 90%, 95%, 96%, 97%, 98% or 99% identical to the sequences set forth above.

As used herein, the percent identity between the two sequences is a function of the number of identical positions shared by the sequences (i.e., % identity equals number of identical positions/total number of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

Additionally or alternatively, the protein sequences of the present invention can further be used as a "query sequence" to perform a search against public databases to, for example, identify related sequences. For example, such searches can be performed using the BLAST program (version 2.0) of Altschul, et al., 1990 J. Mol. Biol. 215:403-10.

In certain embodiments, an antibody or antigen-binding moiety of the invention has a heavy chain variable region comprising CDR1, CDR2, and CDR3 sequences and a light chain variable region comprising CDR1, CDR2, and CDR3 sequences, wherein one or more of these CDR sequences have specified amino acid sequences based on the antigen-binding moiety and antibodies described herein or conservative modifications thereof, and wherein the antibodies retain the desired functional properties of the NS2B-NS3 proteinase-binding antigen-binding moieties of the invention. Accordingly, the invention provides an isolated monoclonal antibody, or a functional antigen binding fragment thereof, consisting of a heavy chain variable region comprising CDR1, CDR2, and CDR3 sequences and a light chain variable region comprising CDR1, CDR2, and CDR3 sequences, wherein: the heavy chain variable region CDR1 amino acid sequences are selected from the group consisting of SEQ ID NOs: 2, 10, 18, 26, 34, 42, and 50, and conservative modifications thereof; the heavy chain variable region CDR2 amino acid sequences are selected from the group consisting of SEQ ID NOs: 3, 11, 19, 27, 35, 43, and 51, and conservative modifications thereof; the heavy chain variable region CDR3 amino acid sequences are selected from the group consisting of SEQ ID NOs: 4, 12, 20, 28, 36, 44, and 52, and conservative modifications thereof; the light chain variable regions CDR1 amino acid sequences are selected from the group consisting of SEQ ID NOs: 6, 14, 22, 30, 38, 46, and 54, and conservative modifications thereof; the light chain variable regions CDR2 amino acid sequences are selected from the group consisting of SEQ ID NOs: 7, 15, 23, 31, 39, 47, and 55, and conservative modifications thereof; the light chain variable regions of CDR3 amino acid sequences are selected from the group consisting of SEQ ID NOs: 8, 16, 24, 32, 40, 48, and 56, and conservative modifications thereof; the antibody or the antigen-binding fragment thereof specifically bind to NS2B-NS3 proteinase of West Nile Virus.

In certain aspects, the invention provides an isolated antigen-binding moiety having: a full length heavy chain comprising an amino acid sequence that has been optimized for expression in the cell of a mammalian selected from the group consisting of SEQ ID NOs: 1, 9, 17, 25, 33, 41 and 49; and a full length light chain comprising an amino acid sequence that has been optimized for expression in the cell of a mammalian selected from the group consisting of SEQ ID NOs: 5, 13, 21, 29, 37, 45, and 53. In certain specific aspects, the isolated antigen-binding moiety is an isolated monoclonal antibody.

In another aspect, the present invention provides NS2B-NS3 proteinase-binding antigen-binding moieties that comprise the heavy chain and light chain CDR1s, CDR2s and CDR3s as described in Table 2, or combinations thereof. The amino acid sequences of the VH CDR1s of are shown in SEQ ID NOs: 2, 10, 18, 26, 34, 42, and 50. The amino acid sequences of the VH CDR2s of the antibodies and are shown in SEQ ID NOs: 3, 11, 19, 27, 35, 43, and 51. The amino acid sequences of the VH CDR3s of the antibodies are shown in SEQ ID NOs: 4, 12, 20, 28, 36, 44, and 52. The amino acid sequences of the VL CDR1s of the antibodies are shown in SEQ ID NOs: 6, 14, 22, 30, 38, 46, and 54. The amino acid sequences of the VL CDR2s of the antibodies are shown in SEQ ID NOs: 7, 15, 23, 31, 39, 47, and 55. The amino acid sequences of the VL CDR3s of the antibodies are shown in SEQ ID NOs: 8, 16, 24, 32, 40, 48, and 56. The CDR regions are delineated using the Kabat system (Kabat, E. A., et al., 1991 Sequences of Proteins of Immunological Interest, Fifth Edition, U.S. Department of Health and Human Services, NIH Publication No. 91-3242).

Given that each of these antigen-binding moieties can bind to NS2B-NS3 proteinase of West Nile Virus and that antigen-binding specificity is provided primarily by the CDR1, 2 and 3 regions, the VH CDR1, 2 and 3 sequences and VL CDR1, 2 and 3 sequences can be "mixed and matched" (i.e., CDRs from different antigen-binding moieties can be mixed and match. For antibodies, each antibody must contain a VH CDR1, 2 and 3 and a VL CDR1, 2 and 3 to create other NS2B-NS3 proteinase-binding binding molecules of the invention. Such "mixed and matched" NS2B-NS3 proteinase-binding antibodies can be tested using the binding assays known in the art and those described in the Examples (e.g., ELISAs). When VH CDR sequences are mixed and matched, the CDR1, CDR2 and/or CDR3 sequence from a particular VH sequence should be replaced with a structurally similar CDR sequence(s). Likewise, when VL CDR sequences are mixed and matched, the CDR1, CDR2 and/or CDR3 sequence from a particular VL sequence should be replaced with a structurally similar CDR sequence(s). It will be readily apparent to the ordinarily skilled artisan that novel VH and VL sequences can be created by substituting one or more VH and/or VL CDR region sequences with structurally similar sequences from the CDR sequences shown herein for monoclonal antibodies of the present invention.

Accordingly, the present invention provides an isolated antigen-binding moieties comprising a heavy chain variable region CDR1 comprising an amino acid sequence selected from the group consisting of SEQ ID NOs: 2, 10, 18, 26, 34, 42, and 50; a heavy chain variable region CDR2 comprising an amino acid sequence selected from the group consisting of SEQ ID NOs: 3, 11, 19, 27, 35, 43, and 51; a heavy chain variable region CDR3 comprising an amino acid sequence selected from the group consisting of SEQ ID NOs: 4, 12, 20, 28, 36, 44, and 52; a light chain variable region CDR1 comprising an amino acid sequence selected from the group consisting of SEQ ID NOs: 6, 14, 22, 30, 38, 46, and 54; a light chain variable region CDR2 comprising an amino acid sequence selected from the group consisting of SEQ ID NOs: 7, 15, 23, 31, 39, 47, and 55; and a light chain variable region CDR3 comprising an amino acid sequence selected from the group consisting of SEQ ID NOs: 8, 16, 24, 32, 40, 48, and 56; wherein the antibody specifically binds NS2B-NS3 proteinase of West Nile Virus.

In a specific embodiment, an antigen-binding moiety or an antibody that specifically binds to NS2B-NS3 proteinase of West Nile Virus comprises a heavy chain variable region CDR1 of SEQ ID NO: 2; a heavy chain variable region CDR2 of SEQ ID NO: 3; a heavy chain variable region CDR3 of SEQ ID NO: 4; a light chain variable region CDR1 of SEQ ID NO: 6; a light chain variable region CDR2 of SEQ ID NO: 7; and a light chain variable region CDR3 of SEQ ID NO: 8.

In another specific embodiment, an antigen-binding moiety or an antibody that specifically binds to NS2B-NS3 proteinase of West Nile Virus comprises a heavy chain variable region CDR1 of SEQ ID NO: 10; a heavy chain variable region CDR2 of SEQ ID NO: 11; a heavy chain variable region CDR3 of SEQ ID NO: 12; a light chain variable region CDR1 of SEQ ID NO: 14; a light chain variable region CDR2 of SEQ ID NO: 15; and a light chain variable region CDR3 of SEQ ID NO: 16.

In another specific embodiment, an antigen-binding moiety or an antibody that specifically binds to NS2B-NS3 proteinase of West Nile Virus comprises a heavy chain variable region CDR1 of SEQ ID NO: 18; a heavy chain variable region CDR2 of SEQ ID NO: 19; a heavy chain variable region CDR3 of SEQ ID NO: 20; a light chain variable region CDR1 of SEQ ID NO: 22; a light chain variable region CDR2 of SEQ ID NO: 23; and a light chain variable region CDR3 of SEQ ID NO: 24.

In another specific embodiment, an antigen-binding moiety or an antibody that specifically binds to NS2B-NS3 proteinase of West Nile Virus comprises a heavy chain variable region CDR1 of SEQ ID NO: 26; a heavy chain variable region CDR2 of SEQ ID NO: 27; a heavy chain variable region CDR3 of SEQ ID NO: 28; a light chain variable region CDR1 of SEQ ID NO: 30; a light chain variable region CDR2 of SEQ ID NO: 31; and a light chain variable region CDR3 of SEQ ID NO: 32.

In another specific embodiment, an antigen-binding moiety or an antibody that specifically binds to NS2B-NS3 proteinase of West Nile Virus comprises a heavy chain variable region CDR1 of SEQ ID NO: 34; a heavy chain variable region CDR2 of SEQ ID NO: 35; a heavy chain variable region CDR3 of SEQ ID NO: 36; a light chain variable region CDR1 of SEQ ID NO: 38; a light chain variable region CDR2 of SEQ ID NO: 39; and a light chain variable region CDR3 of SEQ ID NO: 40.

In another specific embodiment, an antigen-binding moiety or an antibody that specifically binds to NS2B-NS3 proteinase of West Nile Virus comprises a heavy chain variable region CDR1 of SEQ ID NO: 42; a heavy chain variable region CDR2 of SEQ ID NO: 43; a heavy chain variable region CDR3 of SEQ ID NO: 44; a light chain variable region CDR1 of SEQ ID NO: 46; a light chain variable region CDR2 of SEQ ID NO: 47; and a light chain variable region CDR3 of SEQ ID NO: 48.

In another specific embodiment, an antigen-binding moiety or an antibody that specifically binds to NS2B-NS3 proteinase of West Nile Virus comprises a heavy chain variable region CDR1 of SEQ ID NO: 50; a heavy chain variable region CDR2 of SEQ ID NO: 51; a heavy chain variable region CDR3 of SEQ ID NO: 52; a light chain variable region CDR1 of SEQ ID NO: 54; a light chain variable region CDR2 of SEQ ID NO: 55; and a light chain variable region CDR3 of SEQ ID NO: 56.

The present invention provides isolated antigen-binding moieties comprising a H-CDR3 region selected from anyone of the H-CDR3 regions shown in Table 2. The present invention also provides antigen-binding moieties further comprising a H-CDR1 region selected from anyone of the H-CDR1 regions shown in Table 2 and/or a H-CDR2 region selected from anyone of the H-CDR2 regions shown in Table 2. The present invention also provides antigen-binding moieties comprising a heavy chain variable region selected from anyone of the heavy chain variable (VH) regions shown in Table 2.

The present invention provides isolated antigen-binding moieties comprising a L-CDR1 region selected from anyone of the L-CDR1 regions shown in Table 2 and/or a L-CDR2 region selected from anyone of the L-CDR2 regions shown in Table 2 and/or a L-CDR3 region selected from anyone of the L-CDR3 regions shown in Table 2. The present invention also provides antigen-binding moieties comprising a light chain variable region selected from anyone of the light chain variable (VL) regions shown in Table 2.

The present invention also provides antigen-binding moieties with improved properties, for example antigen-binding moieties with higher affinity to the target peptide, i.e. NS2B-NS3 proteinase of West Nile Virus. The present application describes antigen-binding moieties with such improved properties. See Example 4.

In specific embodiments the present invention provides antigen-binding moieties as described herein above, wherein said antigen-binding moiety comprises a H-CDR3 region selected from the group consisting of SEQ ID NOs: 57-63. In these antigen-binding moieties the H-CDR3 region of AbD5323 (SEQ ID.: 28) is replaced by anyone of SEQ ID NOs. 57-71. Therefore, in certain specific embodiments the present invention provides antigen-binding moieties as described herein above, wherein the leucine residue at position 108 of the variable heavy chain of AbD05323 is replaced by arginine. In other specific embodiments the present invention provides antigen-binding moieties as described herein above, wherein the asparagines residue at position 109 of the variable heavy chain of AbD05323 is replaced by arginine. In other specific embodiments the present invention provides antigen-binding moieties as described herein above, wherein the aspartic acid residue at position 110 of the variable heavy chain of AbD05323 is replaced by alanine. In other specific embodiments the present invention provides antigen-binding moieties as described herein above, wherein the aspartic acid residue at position 110 of the variable heavy chain of AbD05323 is replaced by serine. In other specific embodiments the present invention provides antigen-binding moieties as described herein above, wherein the aspartic acid residue at position 110 of the variable heavy chain of AbD05323 is replaced by glycine. In other specific embodiments the present invention provides antigen-binding moieties as described herein above, wherein the leucine residue at position 108 of the variable heavy chain of AbD05323 is replaced by arginine, the asparagines residue at position 109 is replaced by arginine and the aspartic acid residue at position 110 is replaced by alanine. In other specific embodiments the present invention provides antigen-binding moieties as described herein above, wherein the leucine residue at position 108 of the variable heavy chain of AbD05323 is replaced by arginine, the asparagines residue at position 109 is replaced by arginine and the aspartic acid residue at position 110 is replaced by serine. In other specific embodiments the present invention provides antigen-binding moieties as described herein above, wherein the leucine residue at position 108 of the variable heavy chain of AbD05323 is replaced by arginine, the asparagines residue at position 109 is replaced by arginine and the aspartic acid residue at position 110 is replaced by glycine.

In certain embodiments the present invention provides antigen-binding moieties having an Ki of less than 300 nM against wild type NS2B-NS3 proteinase of West Nile Virus. Preferably said antigen-binding moieties have an Ki of less than 200 nM, less than 100 nM, less than 75 nM or less than 50 nM against wild type NS2B-NS3 proteinase of West Nile Virus.

In certain embodiments the present invention provides antigen-binding moieties, wherein the Ki of said antigen-binding moieties against wild type NS2B-NS3 proteinase of West Nile Virus is at least 3-fold lower than the Ki against a T52V mutant of NS2B-NS3 proteinase of West Nile Virus. Preferably said Ki against a T52V mutant of NS2B-NS3 proteinase of West Nile Virus is at least 5-fold, at least 10-fold or at least 20-fold lower.

In certain embodiments the present invention provides antigen-binding moieties, wherein the Ki of said antigen-binding moieties against wild type NS2B-NS3 proteinase of West Nile Virus is at least 3-fold lower than the Ki against a R76L mutant of NS2B-NS3 proteinase of West Nile Virus. Preferably said Ki against a R76L mutant of NS2B-NS3 proteinase of West Nile Virus is at least 5-fold, at least 10-fold or at least 20-fold lower.

In certain embodiments the present invention provides antigen-binding moieties, wherein the Ki of said antigen-binding moieties against wild type NS2B-NS3 proteinase of West Nile Virus is at least 3-fold lower than the Ki against a H51A mutant of NS2B-NS3 proteinase of West Nile Virus. Preferably said Ki against a H51A mutant of NS2B-NS3 proteinase of West Nile Virus is at least 5-fold, at least 10-fold or at least 20-fold lower.

In other embodiments, an antigen-binding moiety or antibody of the invention optimized for expression in a mammalian cell has a full length heavy chain sequence and a full length light chain sequence, wherein one or more of these sequences have specified amino acid sequences based on the antigen-binding moieties described herein or conservative modifications thereof, and wherein the antibodies retain the desired functional properties of the NS2B-NS3 proteinase-binding antigen-binding moieties of the invention. Accordingly, the invention provides an isolated antigen-binding moiety or an isolated monoclonal antibody optimized for expression in a mammalian cell consisting of a full length heavy chain and a full length light chain wherein: the full length heavy chain has amino acid sequences selected from the group of SEQ ID NOs: 1, 9, 17, 25, 33, 41 and 49, and conservative modifications thereof; and the full length light chain has amino acid sequences selected from the group of SEQ ID NOs: 5, 13, 21, 29, 37, 45, and 53, and conservative modifications thereof; the antibody specifically binds to NS2B-NS3 proteinase of West Nile Virus.

The present invention provides antigen-binding moieties that bind to the same epitope as do the NS2B-NS3 proteinase-binding antigen-binding moieties described in the present application. Additional antibodies can therefore be identified based on their ability to cross-compete (e.g., to competitively inhibit the binding of, in a statistically significant manner)

with other antigen-binding moieties of the invention in NS2B-NS3 proteinase-binding assays. The ability of a test antibody to inhibit the binding of antigen-binding moieties of the present invention to NS2B-NS3 proteinase of West Nile Virus demonstrates that the test antigen-binding moieties can compete with that antibody for binding to NS2B-NS3 proteinase; such an antigen-binding moiety may, according to non-limiting theory, bind to the same or a related (e.g., a structurally similar or spatially proximal) epitope on the NS2B-NS3 proteinase of West Nile Virus as the antigen-binding moiety with which it competes. In a certain embodiment, the antibody that binds to the same epitope on NS2B-NS3 proteinase of West Nile Virus as the antigen-binding moieties of the present invention is a human monoclonal antibody. Such human monoclonal antibodies can be prepared and isolated as described herein. In certain embodiments the antigen-binding moiety of the present invention competes for binding to an epitope with an antigen-binding moiety, an antibody, or an antibody fragment according specifically disclosed in the present invention.

An antigen-binding moiety or antibody of the invention further can be prepared using an antigen-binding moiety or antibody having one or more of the VH and/or VL sequences shown herein as starting material to engineer a modified antibody, which modified antibody may have altered properties from the starting antibody. An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody. One type of variable region engineering that can be performed is CDR grafting. Another type of variable region modification is to mutate amino acid residues within the VH and/or VL CDR1, CDR2 and/or CDR3 regions to thereby improve one or more binding properties (e.g., affinity) of the antibody of interest, known as "affinity maturation." Respective technologies that may be employed are well know to the skilled artisan.

The antigen-binding moieties and antibodies of the present invention may also be bispecific or multispecific molecules comprising an NS2B-NS3 proteinase-binding antigen-binding moiety of the invention. Accordingly, the present invention includes bispecific molecules comprising at least one first binding specificity for NS2B-NS3 proteinase of West Nile Virus and a second binding specificity for a second target epitope. For example, the second target epitope is another epitope of NS2B-NS3 proteinase of West Nile Virus different from the first target epitope. Additionally, for the invention in which the bispecific molecule is multi-specific, the molecule can further include a third binding specificity, in addition to the first and second target epitope. In one embodiment, the bispecific molecules of the invention comprise as a binding specificity at least one antibody, or an antibody fragment thereof, including, e.g., an Fab, Fab', F(ab')2, Fv, or a single chain Fv. The antibody may also be a light chain or heavy chain dimer, or any minimal fragment thereof such as a Fv or a single chain construct as described in Ladner et al. U.S. Pat. No. 4,946,778. Other bivalent, bispecific molecules that might be used are diabodies (Holliger et al., 1993 Proc. Natl. Acad. Sci. USA 90:6444-6448; Poljak et al., 1994 Structure 2:1121-1123)

The present invention provides for antigen-binding moieties that specifically bind to NS2B-NS3 proteinase of West Nile Virus which have an extended half-life in vivo. Techniques that may be employed include chemical linkage to polyethyleneglycol (PEG), reCODE PEG, antibody scaffold, polysialic acid (PSA), hydroxyethyl starch (HES), albumin-binding ligands, and carbohydrate shields; genetic fusion to proteins binding to serum proteins, such as albumin, IgG, FcRn, and transferring; coupling (genetically or chemically) to other binding moieties that bind to serum proteins, such as nanoboies, Fabs, DARPins, avimers, affibodies, and anticalins; genetic fusion to rPEG, albumin, domain of albumin, albumin-binding proteins, and Fc; or incorporation into nancarriers, slow release formulations, or medical devices.

The present invention provides antigen-binding moieties, antibodies or fragments thereof that specifically bind to NS2B-NS3 proteinase of West Nile Virus recombinantly fused or chemically conjugated (including both covalent and non-covalent conjugations) to a heterologous protein or polypeptide (or fragment thereof, preferably to a polypeptide of at least 10, at least 20, at least 30, at least 40, at least 50, at least 60, at least 70, at least 80, at least 90 or at least 100 amino acids) to generate fusion proteins. In particular, the invention provides fusion proteins comprising an antigen-binding moiety described herein (e.g., a Fab fragment, Fd fragment, Fv fragment, F(ab)2 fragment, a VH domain, a VH CDR, a VL domain or a VL CDR) and a heterologous protein, polypeptide, or peptide. Methods for fusing or conjugating proteins, polypeptides, or peptides to an antibody or an antibody fragment are known in the art. See, e.g., U.S. Pat. Nos. 5,336,603, 5,622,929, 5,359,046, 5,349,053, 5,447,851, and 5,112,946; European Patent Nos. EP 307,434 and EP 367,166; International Publication Nos. WO 96/04388 and WO 91/06570; Ashkenazi et al., 1991, Proc. Natl. Acad. Sci. USA 88: 10535-10539; Zheng et al., 1995, J. Immunol. 154:5590-5600; and Vil et al., 1992, Proc. Natl. Acad. Sci. USA 89:11337-11341.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793, 5,811,238, 5,830,721, 5,834,252, and 5,837,458; Patten et al., 1997, Curr. Opinion Biotechnol. 8:724-33; Harayama, 1998, Trends Biotechnol. 16(2):76-82; Hansson, et al., 1999, J. Mol. Biol. 287:265-76; and Lorenzo and Blasco, 1998, Biotechniques 24(2):308-313 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. A polynucleotide encoding an antibody or fragment thereof that specifically binds to NS2B-NS3 proteinase of West Nile Virus may be recombined with one or more components, motifs, sections, parts, domains, fragments, etc. of one or more heterologous molecules.

Moreover, the antigen-binding moieties or antibodies of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA 86:821-824, for instance, hexa-histidine provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37:767), and the "flag" tag.

In other embodiments, antigen-binding moieties or antibodies of the present invention or fragments thereof conjugated to a diagnostic or detectable agent. Such antibodies can be useful for monitoring or prognosing the onset, development, progression and/or severity of a disease or disorder as part of a clinical testing procedure, such as determining the efficacy of a particular therapy. Such diagnosis and detection can accomplished by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine (131I, 125I, 123I, and 121I), carbon (14C), sulfur (35S), tritium (3H), indium (115In, 113In, 112In, and 111In), technetium (99Tc), thallium (201Ti), gallium (68Ga, 67Ga), palladium (103Pd), molybdenum (99Mo), xenon (133Xe), fluorine (18F), 153Sm, 177Lu, 159Gd, 149Pm, 140La, 175Yb, 166Ho, 90Y, 47Sc, 186Re, 188Re, 142Pr, 105Rh, 97Ru, 68Ge, 57Co, 65Zn, 85Sr, 32P, 153Gd, 169Yb, 51Cr, 54Mn, 75Se, 113Sn, and 117Tin; and positron emitting metals using various positron emission tomographies, and nonradioactive paramagnetic metal ions.

The present invention further encompasses uses of antigen-binding moieties, antibodies or fragments thereof conjugated to a therapeutic moiety. An antibody or fragment thereof may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells.

Further, an antigen-binding moieties, antibody or fragment thereof may be conjugated to a therapeutic moiety or drug moiety that modifies a given biological response. Therapeutic moieties or drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, pseudomonas exotoxin, cholera toxin, or diphtheria toxin; a protein such as tumor necrosis factor, α-interferon, β-interferon, nerve growth factor, platelet derived growth factor, tissue plasminogen activator, an apoptotic agent, an anti-angiogenic agent; or, a biological response modifier such as, for example, a lymphokine.

Moreover, an antigen-binding moieties or antibody can be conjugated to therapeutic moieties such as a radioactive metal ion, such as alpha-emitters such as 213Bi or macrocyclic chelators useful for conjugating radiometal ions, including but not limited to, 131 In, 131 LU, 131Y, 131 Ho, 131 Sm, to polypeptides. In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., 1998, Clin Cancer Res. 4(10):2483-90; Peterson et al., 1999, Bioconjug. Chem. 10(4):553-7; and Zimmerman et al., 1999, Nucl. Med. Biol. 26(8):943-50, each incorporated by reference in their entireties.

Moreover, an antigen-binding moiety or antibody can be conjugated to a moiety wherein said moiety triggers, enables or facilitates internalization of the antigen-binding moiety or antibody into a host cell infected with West Nile Virus. Respective peptides or domains are known in the art. See for example Cancer Biother Radiopharm. 2008 February; 23(1): 3-24; Curr Pharm Des. 2008; 14(24):2415-47; Cell Mol Life Sci. 2005 August; 62(16):1839-49 and Adv Drug Deliv Rev. 2005 Feb. 28; 57(4):637-51.

Techniques for conjugating therapeutic moieties to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, Immunol. Rev. 62:119-58.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

As used herein, the term "affinity" refers to the strength of interaction between a molecule comprising an antigen-binding moiety and an antigen at single antigenic sites. Within each antigenic site, the variable region of the antibody "arm" interacts through weak non-covalent forces with antigen at numerous sites; the more interactions, the stronger the affinity.

The term "binding specificity" as used herein refers to the ability of an individual antibody combining site to react with only one antigenic determinant. The combining site of the antibody is located in the Fab portion of the molecule and is constructed from the hypervariable regions of the heavy and light chains. Binding affinity of an antibody is the strength of the reaction between a single antigenic determinant and a single combining site on the antibody. It is the sum of the attractive and repulsive forces operating between the antigenic determinant and the combining site of the antibody. The phrases "an antigen-binding moiety recognizing an antigen" and "an antigen-binding specific for an antigen" are used interchangeably herein with the term "an antigen-binding which binds specifically to an antigen".

The terms "NS2B-NS3 proteinase" and "NS2B-NS3" are used interchangeably, and refer to the viral two component system encoded by West Nile Virus. "NS2B" refers to the essential cofactor of NS3pro of West Nile Virus. The primary amino acid sequences of NS2B from two strains of West Nile Virus are shown in FIG. 1. "NS3pro" and "NS3 proteinase" are used interchangeably, and refer to the West Nile Virus protein exhibiting proteinase activity. The primary amino acid sequences of NS3pro from two strains of West Nile Virus are shown in FIG. 1.

The terms "West Nile virus" or "WNV" are used herein interchangeably. WNV, the causative agent of West Nile fever, is a virus of the family Flaviviridae. The term is art recognized.

In certain aspects of the present invention the antigen-binding moieties of the present invention specifically bind to NS2B-NS3 proteinase of West Nile Virus. In other aspects the antigen-binding moieties of the present invention specifically bind to NS3 polypeptide of West Nile Virus. In yet other aspects the antigen-binding moieties of the present invention specifically bind to NS3pro domain of the NS3 polypeptide of West Nile Virus. The NS3pro domain corresponds to about the N-terminal 184 amino acid residues of the full length NS3 polypeptide (Current Medicinal Chemistry, Volume 15, Number 27, November 2008, pp. 2771-2784). Therefore, in certain aspects of the present invention the antigen-binding moieties of the present invention specifically bind to the N-terminal 184 amino acid residues of the full length NS3 polypeptide of West Nile Virus.

In certain aspects of the present invention the antigen-binding moieties specifically bind to the active site of NS2B-NS3 proteinase of West Nile Virus. The active site of NS2B-NS3 proteinase of West Nile Virus was studied in detail. Some of the key publications include J. Virol. 2003 July; 77(14): 7804-13, J Biol. Chem. 2005 Jan. 28; 280(4):2896-903, J Biol. Chem. 2006 Dec. 15; 281(50):38448-58, Biol. Chem., Apr. 27, 2007; 282(17): 12883-12892, J. Virol., May 1, 2007; 81(9): 4501-4509, & J Gen Virol. 2008 March; 89(Pt 3):636-41.

In certain aspects of the present invention the antigen-binding moieties inhibits the enzymatic activity of NS2B-NS3 proteinase of West Nile Virus. As will be appreciated, amino acid residues which are essential for the enzymatic activity of NS2B-NS3 proteinase of West Nile Virus can readily be deduced from the publications recited in the preceding paragraph.

In certain aspects of the present invention the antigen-binding moieties bind to wild type NS2B-NS3 proteinase of West Nile Virus but not to an active site mutant of NS2B-NS3 proteinase of West Nile Virus. Such active site mutants include, but are not limited to H51A, T52V and/or R76L mutants of NS2B-NS3 proteinase of West Nile Virus. Therefore, in certain aspects of the present invention the antigen-binding moieties bind to wild type NS2B-NS3 proteinase of West Nile Virus but not to a H51A mutant of NS2B-NS3 proteinase. In other aspects of the present invention the antigen-binding moieties bind to wild type NS2B-NS3 proteinase of West Nile Virus but not to a T52V mutant of NS2B-NS3 proteinase. In other aspects of the present invention the antigen-binding moieties bind to wild type NS2B-NS3 proteinase of West Nile Virus but not to a R76L mutant of NS2B-NS3 proteinase. In other aspects of the present invention the antigen-binding moieties bind to wild type NS2B-NS3 proteinase of West Nile Virus but not to a H51A mutant and not to a T52V mutant of NS2B-NS3 proteinase. In other aspects of the present invention the antigen-binding moieties bind to wild type NS2B-NS3 proteinase of West Nile Virus but not to a H51A mutant and not to a R76L mutant of NS2B-NS3 proteinase. In other aspects of the present invention the antigen-binding moieties bind to wild type NS2B-NS3 proteinase of West Nile Virus but not to a T52V mutant and not to a R76L mutant of NS2B-NS3 proteinase. In other aspects of the present invention the antigen-binding moieties bind to wild type NS2B-NS3 proteinase of West Nile Virus but not to a not to a H51A mutant, not to a T52V mutant and not to a R76L mutant of NS2B-NS3 proteinase.

In certain aspects of the present invention the antigen-binding moieties specifically bind to NS2B-NS3 proteinase of strain NY99 of West Nile Virus. In certain aspects of the present invention the antigen-binding moieties specifically bind to the active site of NS2B-NS3 proteinase of strain NY99 of West Nile Virus. In certain aspects of the present invention the antigen-binding moieties inhibit the enzymatic activity of NS2B-NS3 proteinase of strain NY99 of West Nile Virus.

In certain aspects of the present invention the antigen-binding moieties specifically bind to NS2B-NS3 proteinase of strain DV of West Nile Virus. In certain aspects of the present invention the antigen-binding moieties specifically bind to the active site of NS2B-NS3 proteinase of strain DV of West Nile Virus. In certain aspects of the present invention the antigen-binding moieties inhibit the enzymatic activity of NS2B-NS3 proteinase of strain DV of West Nile Virus.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some embodiments, the term "conservative sequence modifications" are used to refer to amino acid modifications that do not significantly affect or alter the binding characteristics of the antibody containing the amino acid sequence.

The terms "identical" or percent "identity," in the context of two or more nucleic acids or polypeptide sequences, refer to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection.

Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

As used herein, the term "high affinity" for an IgG antibody refers to an antibody having a KD of $10^{-8}$ M or less, $10^{-9}$ M or less, or $10^{-10}$ M, or $10^{-11}$ M or less for a target antigen. However, "high affinity" binding can vary for other antibody isotypes. For example, "high affinity" binding for an IgM isotype refers to an antibody having a KD of $10^{-7}$ M or less, or $10^{-8}$ M or less.

The term "Kassoc" or "Ka", as used herein, is intended to refer to the association rate of a particular antibody-antigen interaction (or general a binder-ligand interaction), whereas the term "Kdis" or "Kd," as used herein, is intended to refer to the dissociation rate of a particular antibody-antigen interaction. The term "$K_D$", as used herein, is intended to refer to the dissociation constant, which is obtained from the ratio of Kd to Ka (i.e. Kd/Ka) and is expressed as a molar concentration (M). $K_D$ values for antibodies can be determined using methods well established in the art. A method for determining the $K_D$ of an antibody is by using surface plasmon resonance, or using a biosensor system such as a Biacore® system. For inhibitory antibodies the term "Ki" or "$K_i$" is used. "Ki" or "$K_i$" is equivalent to term "$K_D$", but is, as mentioned, generally only used for inhibitory molecules, such as the antibodies of the present invention.

The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

The term "treating" includes the administration of compositions or antibodies to prevent or delay the onset of the symptoms, complications, or biochemical indicia of a disease (e.g., AMD), alleviating the symptoms or arresting or inhibiting further development of the disease, condition, or disorder. Treatment may be prophylactic (to prevent or delay the onset of the disease, or to prevent the manifestation of clinical or subclinical symptoms thereof) or therapeutic suppression or alleviation of symptoms after the manifestation of the disease.

The present invention provides antigen-binding moieties that specifically bind to NS2B-NS3 proteinase of West Nile Virus, pharmaceutical compositions, production methods, and methods of use of such antigen-binding moieties and compositions.

The present invention provides antigen-binding moieties that specifically bind to NS2B-NS3 proteinase of West Nile Virus, said antigen-binding moieties comprising a VH domain having an amino acid sequence of anyone of SEQ ID NOs: 1, 9, 17, 25, 33, 41 or 49. The present invention also provides antigen-binding moieties that specifically bind to NS2B-NS3 proteinase of West Nile Virus, said antigen-binding moieties comprising a VH CDR having an amino acid sequence of any one of the VH CDRs listed in Table 2. In particular, the invention provides antigen-binding moieties that specifically bind to NS2B-NS3 proteinase of West Nile Virus, said antigen-binding moieties comprising (or alternatively, consisting of) one, two, three, four, five or more VH CDRs having an amino acid sequence of any of the VH CDRs listed in Table 2.

The present invention provides antigen-binding moieties that specifically bind to NS2B-NS3 proteinase of West Nile Virus, said antigen-binding moieties comprising a VL domain having an amino acid sequence of anyone of SEQ ID NOs: 5, 13, 21, 29, 37, 45, or 53. The present invention also provides antigen-binding moieties that specifically bind to NS2B-NS3 proteinase of West Nile Virus, said antigen-binding moieties comprising a VL CDR having an amino acid sequence of any one of the VL CDRs listed in Table 2. In particular, the invention provides antigen-binding moieties that specifically bind to NS2B-NS3 proteinase of West Nile Virus, said antigen-binding moieties comprising (or alternatively, consisting of) one, two, three, four, five or more VL CDRs having an amino acid sequence of any of the VL CDRs listed in Table 2.

Other antigen-binding moieties of the invention include amino acids that have been mutated, yet have at least 60, 70, 80, 90 or 95 percent identity in the CDR regions with the CDR regions shown in Table 2. In some embodiments, it includes mutant amino acid sequences wherein no more than 1, 2, 3, 4 or 5 amino acids have been mutated in the CDR regions when compared with the CDR regions shown in Table 2.

The present invention also provides nucleic acid sequences that encode VH, VL, the full length heavy chain, and the full length light chain of the antigen-binding moieties or the antibodies that specifically bind to NS2B-NS3 proteinase of West Nile Virus. Such nucleic acid sequences can be optimized for expression in mammalian cells.

Other antigen-binding moieties of the invention include those where the amino acids or nucleic acids encoding the amino acids have been mutated, yet have at least 60, 70, 80, 90 or 95 percent identity to the sequences shown in Table 2. In some embodiments, it include mutant amino acid sequences wherein no more than 1, 2, 3, 4 or 5 amino acids have been mutated in the variable regions when compared with the variable regions depicted in the sequence shown in Table 2, while retaining substantially the same therapeutic or diagnostic activity.

The present invention provides methods of treating a subject infected with West Nile Virus by administering to a subject in need thereof an effective amount of the antigen-binding moiety of the invention.

In certain embodiments the present invention provides methods of reducing or eliminating the symptoms of a subject infected with West Nile Virus by administering to a subject in need thereof an effective amount of the antigen-binding moiety of the invention.

Subjects to be treated with therapeutic agents of the present invention can also be administered other therapeutic agents with know methods of treating conditions associated with West Nile Virus infection. When the therapeutic agents of the present invention are administered together with another agent, the two can be administered sequentially in either order or simultaneously. In some aspects, an antigen-binding moiety of the present invention is administered to a subject who is also receiving therapy with a second agent.

In certain embodiments the present invention provides the use of an antigen-binding moiety, an antibody, or an antibody fragment according to the present invention for the prophylaxis or treatment of an infection with West Nile Virus. In other embodiments the present invention provides a method for preventing or treating an infection with West Nile Virus, said method comprising administering an antigen-binding moiety, an antibody, or an antibody fragment according to the present invention to a patient infected or suspected to be infected with West Nile Virus.

In one aspect, the invention encompasses diagnostic assays for determining NS2B-NS3 proteinase and/or nucleic acid expression as well as NS2B-NS3 proteinase function, in the context of a biological sample (e.g., blood, serum, cells, tissue) or from individual is afflicted with a disease or disorder, or is at risk of developing a disorder associated with West Nile Virus infection.

In certain aspects the present invention provides the use of an antigen-binding moiety, an antibody, or an antibody fragment according to the present invention for diagnosing or monitoring infection with West Nile Virus. In other aspects the present invention provides a method for diagnosing or monitoring an infection with West Nile Virus, said method comprising detecting West Nile Virus via an antigen-binding moiety, an antibody, or an antibody fragment of the present invention.

Diagnostic assays, such as competitive assays rely on the ability of a labeled analogue (the "tracer") to compete with the test sample analyte for a limited number of binding sites on a common binding partner. The binding partner generally is insolubilized before or after the competition and then the tracer and analyte bound to the binding partner are separated from the unbound tracer and analyte. This separation is accomplished by decanting (where the binding partner was preinsolubilized) or by centrifuging (where the binding partner was precipitated after the competitive reaction). The amount of test sample analyte is inversely proportional to the amount of bound tracer as measured by the amount of marker substance. Dose-response curves with known amounts of analyte are prepared and compared with the test results in order to quantitatively determine the amount of analyte present in the test sample. These assays are called ELISA systems when enzymes are used as the detectable markers. In an assay of this form, competitive binding between antigen-binding moieties and C5-binding antigen-binding moieties results in the bound NS2B-NS3 proteinase, preferably the NS2B-NS3 proteinase epitopes of the invention, being a measure of antigen-binding moieties in the serum sample, most particularly, neutralising antibodies in the serum sample. A significant advantage of the assay is that measurement is made of neutralising antibodies directly (i.e., those which interfere with binding of NS2B-NS3 proteinase protein, specifically, epitopes). Such an assay, particularly in the form of an ELISA test has considerable applications in the clinical environment and in routine blood screening.

In the clinical diagnosis or monitoring of patients with disorders associated with West Nile Virus infection, the detection of NS2B-NS3 proteinase in comparison to the levels in a corresponding biological sample from a normal subject is indicative of a patient's infection with or exposure to West Nile virus.

The invention also pertains to the field of predictive medicine in which diagnostic assays, prognostic assays, pharmacogenomics, and monitoring clinical trials are used for prognostic (predictive) purposes to thereby treat an individual prophylactically.

The invention also provides for prognostic (or predictive) assays for determining whether an individual is infected with West Nile virus or is at risk of developing symptoms of West Nile Virus infection after exposure to the virus or after having had contact with other subject with West Nile Virus infection. Such assays can be used for prognostic or predictive purpose to thereby prophylactically treat an individual prior to an infection with West Nile Virus.

Another aspect of the invention provides methods for determining NS2B-NS3 proteinase nucleic acid expression or NS2B-NS3 proteinase protein activity in an individual to thereby select appropriate therapeutic or prophylactic agents for that individual (referred to herein as "pharmacogenomics"). Pharmacogenomics allows for the selection of agents (e.g., antigen-binding moieties of the present invention) for therapeutic or prophylactic treatment of an individual based on the genotype of the individual (e.g., the genotype of the individual examined to determine the ability of the individual to respond to a particular agent.)

Yet another aspect of the invention pertains to monitoring the influence of agents (e.g., antigen-binding moieties of the present invention) on the expression or activity of NS2B-NS3 proteinase in clinical trials.

The invention provides pharmaceutical compositions comprising the NS2B-NS3 proteinase-binding antigen-binding moieties (intact or binding fragments) formulated together with a pharmaceutically acceptable carrier. The compositions can additionally contain one or more other therapeutic agents that are suitable for treating or preventing West Nile Virus infection or symptoms associated with West Nile Virus infection. Pharmaceutically carriers enhance or stabilize the composition, or to facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition of the present invention can be administered by a variety of methods known in the art. The route and/or mode of administration vary depending upon the desired results. It is preferred that administration be intravenous, intramuscular, intraperitoneal, or subcutaneous, or administered proximal to the site of the target. The pharmaceutically acceptable carrier should be suitable for intravenous, intramuscular, subcutaneous, parenteral, spinal or epidermal administration (e.g., by injection or infusion). Depending on the route of administration, the active compound, i.e., antigen-binding moiety, antibody, bispecific and multispecific molecule, may be coated in a material to protect the compound from the action of acids and other natural conditions that may inactivate the compound.

The composition should be sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

Pharmaceutical compositions of the invention can be prepared in accordance with methods well known and routinely practiced in the art. See, e.g., Remington: The Science and Practice of Pharmacy, Mack Publishing Co., 20th ed., 2000; and Sustained and Controlled Release Drug Delivery Systems, J. R. Robinson, ed., Marcel Dekker, Inc., New York, 1978. Pharmaceutical compositions are preferably manufactured under GMP conditions. Typically, a therapeutically effective dose or efficacious dose of the NS2B-NS3 proteinase-binding antigen-binding moiety is employed in the pharmaceutical compositions of the invention. The NS2B-NS3 proteinase-binding antigen-binding moieties are formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

A physician or veterinarian can start doses of the antibodies of the invention employed in the pharmaceutical composition at levels lower than that required to achieve the desired therapeutic effect and gradually increase the dosage until the desired effect is achieved. In general, effective doses of the compositions of the present invention, for the treatment of an allergic inflammatory disorder described herein vary depending upon many different factors, including means of administration, target site, physiological state of the patient, whether the patient is human or an animal, other medications administered, and whether treatment is prophylactic or therapeutic. Treatment dosages need to be titrated to optimize safety and efficacy. For systemic administration with an antibody, the dosage ranges from about 0.0001 to 100 mg/kg, and more usually 0.01 to 15 mg/kg, of the host body weight. An exemplary treatment regime entails systemic administration once per every two weeks or once a month or once every 3 to 6 months. For intravitreal administration with an antibody, the dosage ranges from about 0.0001 to about 10 mg. An exemplary treatment regime entails systemic administration once per every two weeks or once a month or once every 3 to 6 months.

Antigen-binding moieties and antibody is usually administered on multiple occasions. Intervals between single dosages can be weekly, monthly or yearly. Intervals can also be irregular as indicated by measuring blood levels of NS2B-NS3 proteinase-binding antigen-binding moiety in the patient. In some methods of systemic administration, dosage is adjusted to achieve a plasma antibody concentration of 1-1000 µg/ml and in some methods 25-500 µg/ml. Alternatively, antigen-binding moiety can be administered as a sustained release formulation, in which case less frequent administration is required. Dosage and frequency vary depending on the half-life of the antigen-binding moiety in the patient. In general, humanized antibodies show longer half life than that of chimeric antibodies and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

EXAMPLES

Reagents were purchased from Sigma-Aldrich (Milwaukee, Wis.) unless indicated otherwise. The pyroglutamic acid-RTKR-7-amino-4-methylcoumarin (Pyr-RTKR-AMC) fluorescence-quenched cleavage peptide was purchased from Bachem (King of Prussia, Pa.). Goat anti-human F(ab')2 fragment conjugated with horseradish peroxidase was from AbD Serotec (Oxford, UK).

Unless indicated otherwise all experimental procedures were performed using standard protocols, essentially as described in Sambrook et al.: Molecular Cloning: A Laboratory Manual, 3 Vol.; Cold Spring Harbor Laboratory (December 2000).

Example 1

Generation of NS2B-NS3 Proteinase Constructs

Earlier studies have indicated that the presence of the 48 residue central NS2B domain linked to the N-terminus of NS3 via a flexible linker (GGGGSGGGG) is required for the catalytic activity of NS3pro (J Biol. Chem. 279, 48535-48542). A K48A mutation in the C-terminal amino acid residue of the NS2B sequence inactivates the autolytic cleavage site. As a result, the NS2BNS3pro K48A mutant is resistant to autoproteolysis and is represented by the intact, single-chain NS2B-NS3pro construct. In another WNV mutant, H51A, the histidine residue at the catalytically essential position 51 is substituted alanine. This H51A mutant is catalytically inert and is not autocleaved.

cDNAs of two WNV strains were used in this study. cDNA of WNV strain NY99 was kindly provided by Drs. Richard Kinney (CDC, Fort Collins, Colo.). cDNA of WNV strain of the DV serotype 2 (DV2; strain 16681) was kindly provided by Michael Diamond (Washington University, St. Louis, Mo.). NS3pro from these two strains share a 50% sequence identity. Although the number of amino acid substitutions proximal to the catalytic triad is minimal, the two proteinases display significant differences in their substrate cleavage preferences, what is also reflected in the sequence and the structure of the active site region.

Strain NY99 has a threonine residue at position 52, whereas strain DV2 has a valine residue at this position. At position 76 strain NY99 has an arginine residue, whereas DV2 has a leucine residue. To explore the potential role of the Thr52 and Arg76 residues, we constructed chimeric proteins with T52V and R76L mutations. Additional mutants we were created in NS2B of NY99—a G22S mutation and a triple DDD/AAA mutation at positions 32-34, a region which might affect either the folding or the interactions of NS2B with NS3pro in the proximity of the active site region or both. Sequence of NS2B and NS3pro for both WNV strains are depicted in FIG. 1, including the mutations generated in the present study.

WNV strain DV2 cDNA was used in PCR reactions followed by routine gene engineering manipulations to generate the DV2 NS2B-NS3pro constructs which included the 48 residue NS2B cofactor (amino acids 1393-1440) linked via a nona-peptide linker GGGGSGGQQ to the NS3pro part (amino acids 1476-1687). Similarly, the NY99 cDNA was used to generate the WNV NS2B-NS3pro constructs which included the 48 residue NS2B cofactor (amino acids 1423-1470) linked via a GGGGSGGGG linker to the NS3pro sequence (amino acids 1506-1689; J. Virol. 81, 4501-4509). The design and purification of the autolytic site-deficient WNV NS2B-NS3pro K48A construct, the H51A, T52V and R76L mutants with the amino acid substitutions in the NS3pro part, and the G22S and Asp32Asp33Asp34/Ala32Ala33Ala34 mutants (DDD/AAA) with the mutations in the NS2B cofactor sequence were described earlier (Protein Expr Purif. 52, 334-339; J. Virol. 81, 4501-4509; J Gen Virol. 89, 636-641). The sequence of the constructs is shown in FIG. 1. The constructs were re-cloned into the pET101/DTOPO expression vector (Invitrogen; Carlsbad/CA).

Competent *E. coli* BL21 CodonPlus (DE3)-RIPL cells (Stratagene) were transformed with the individual recombinant pET101/D-TOPO vectors. Transformed cells were grown in LB broth at 37° C. to reach A600=0.6. Protein expression was then induced at 37° C. using 1 mM isopropyl β-Dthiogalactoside for an additional 6 h. The cells were collected by centrifugation, resuspended in 20 mM Tris-HCl, pH 8.0, containing 1 M NaCl and 1 mg/ml lysozyme and disrupted by sonication. Cell debris was removed by centrifugation. The NY99 and DV2 constructs were purified from the supernatant fraction using HiTrap Co2+-chelating chromatography. The 6×His-tagged NS2B-NS3pro constructs were eluted using a 0-500 mM gradient of imidazole. Fractions were analyzed using SDS-gel electrophoresis followed by Coomassie staining, and also by Western blotting with an anti-6×His antibody (Clontech).

Wild-type DV and NY99 NS2B-NS3pro, as well as NY99/DV chimeras, were expressed in *E. coli* with C-terminal His tags and isolated from the soluble fraction by metal chelating chromatography.

The cleavage kinetics of all constructs were measured in an Pyr-RTKR-AMC cleavage assay, employing a fluorogenic peptide. This assay for NS2B-NS3pro peptide cleavage activity was performed in 0.2 ml 20 mM Tris-HCl buffer, pH 8.0, containing 20% glycerol and 0.005% Brij 35. The cleavage peptide (Pyr-RTKR-AMC) and enzyme concentrations were 25 µM and 10 nM, respectively. Reaction velocity was monitored continuously at $\lambda_{ex}$=360 nm and $\lambda_{em}$=460 nm on a Spectramax Gemini EM fluorescence spectrophotometer (Molecular Devices, Sunnyvale, Calif.). All assays were performed in triplicate in wells of a 96 well plate. The concentration of catalytically active NS2B-NS3pro samples was measured using a fluorescence assay by titration against a standard aprotinin solution (5 nM) (Biochem J. 393, 503-511). The concentration of active NS2B-NS3pro was close to 100% when compared to the protein concentration.

Three of the NY99 mutants K48A, H51A; K48A, G22S and K48A, DDD/AAA had no activity because the G22S and DDD/AAA mutations affect the interactions of the NS2B co-factor with the NS3pro domain and the H51A mutation inactive the proteinase.

TABLE 1

| NS2B-NS3pro | Mean ± SD | | |
|---|---|---|---|
| | $K_m$ (µM) | $k_{cat}$ | $k_{cat}/K_m$ (mM$^{-1}$s$^{-1}$) |
| NY99 wild type | 71 ± 15 | 6.3 ± 0.35 | 88 ± 12 |
| NY99 K48A | 58.8 ± 10 | 5.25 ± 0.25 | 89.3 ± 11 |
| NY99 T52V | 0.13 ± 0.006 | 0.013 ± 0.0006 | 100 ± 10 |
| NY99 R76L | 89 ± 16 | 7.3 ± 0.4 | 82 ± 11 |
| DV2 wild type | 3.6 ± 0.2 | 0.02 ± 0.001 | 5.5 ± 0.5 |
| NY99 K48A, H51A | | No activity | |
| NY99 K48A, G22S | | No activity | |
| NY99 K48A, DDD/AAA | | No activity | |

The purified constructs were used as baits in the antibody selection and characterization procedures.

Example 2

Identification of Binders that Target the Active Site of NS2B-NS3Pro

In this invention a novel screening approach for the generation of high affinity, inhibitory human antibodies that specifically target the active site region was employed. This approach comprises screening against the active site of an enzyme, in the present case a wild-type proteinase. In a second step a counter screen is performed against a mutated, enzymatically non-active form of the enzyme, in the present case a proteinase mutant with a single H51A mutation in the active site. By doing so we successfully isolated selective and potent function-blocking, active site-targeting antibodies to WNV NS2B-NS3pro.

Recombinant antibodies were generated from the HuCAL GOLD collection of human antibody genes (J Mol. Biol. 376, 1182-1200) by three rounds of selection (panning) on immobilized recombinant NS2B-NS3pro protein, as previously described (J Immunol Methods. 275, 203-212; Biol. Chem. 387, 995-1003; J Mol. Biol. 296, 57-86; J Immunol Methods. 254, 67-84; J Biol. Chem. 278, 38194-38205). Prior to selection, the phage library was blocked with NS2B-NS3pro H51A protein in order to deplete antibodies which are specific for epitopes also present on the immobilized antigen.

To identify the Fabs capable of binding the active site region of WNV NS2B-NS3pro we used a bio-panning procedure that involved both the catalytically active NS2B-NS3pro K48A construct with the intact active site sequence and the inert NS2B-NS3pro H51A mutant with the inactivated active site.

First, we identified those Fab clones which efficiently interacted with the NS2B-NS3pro K48A construct. Among these several hundred positive Fabs, we then identified those individual antibodies which did not interact with the H51A active site mutant. As a result of the bio-panning of the HuCAL GOLD library, seven individual antibodies were identified. Results for some of these binders are shown in FIG. 2. All seven binders were capable of binding the wild-type enzyme but incapable of binding the active site mutant. Results for some of these binders are shown in FIG. 2.

After sequencing the DNA inserts, the sequences of the seven individual Fabs (AbD05320, AbD05321, AbD05322, AbD05323, AbD05444, AbD05445 and AbD05446) were determined and the coding sequences were expressed in *E. coli*. Sequences of all heavy and light chains as well as of the CDRs are shown in Table 2. The seven antibodies were isolated from the respective recombinant *E. coli* cells and the purified antibody samples were characterized further.

TABLE 2

| | | SEQ ID NO. |
|---|---|---|
| AbD05320 | | |
| VH | QVQLVQSGAEVKKPGESLKISCKGSGYSFTNYWISWVRQAPGKGL EWMGIIDPGDSDTNYSPSFQGQVTISADKSISTAYLQWSSLKASDT AMYYCARVNYYNFDYWGQGTLVTVSS | 1 |
| H-CDR1 | GYSFTNYWIS | 2 |
| H-CDR2 | WMGIIDPGDSDTNYSPSFQG | 3 |
| H-CDR3 | VNYYNFDY | 4 |
| VL | DIVLTQSPATLSLSPGERATLSCRASQSVTSNLAWYQQKPGQAPRL LIYGNVSRRATGVPARFSGSGSGTDFTLTISSLEPEDFATYYCQQY GDYPATFGQGTKVEIKRT | 5 |
| L-CDR1 | RASQSVTSNLA | 6 |
| L-CDR2 | LLIYGNVSRRAT | 7 |
| L-CDR3 | QQYGDYPA | 8 |
| AbD05321 | | |
| VH | QVQLVQSGAEVKKPGSSVKVSCKASGGTFSSHAISWVRQAPGQG LEWMGGIIPIFGMANYAQKFQGRVTITADESTSTAYMELSSLRSE DTAVYYCARYYWKPVLFDFDVWGQGTLVTVSS | 9 |
| H-CDR1 | GGTFSSHAIS | 10 |
| H-CDR2 | WMGGIIPIFGMANYAQKFQG | 11 |
| H-CDR3 | YYWKPVLFDFDV | 12 |
| VL | DIALTQPASVSGSPGQSITISCTGTSSDIGGNNYVSWYQQHPGKAP KVMIYEVSKRPSGVSNRFSGSKSGNTASLTISGLQAEDEADYYCSS YTMTIFVFGGGTKLTVLGQ | 13 |
| L-CDR1 | TGTSSDIGGNNYVS | 14 |
| L-CDR2 | VMIYEVSKRPS | 15 |
| L-CDR3 | SSYTMTIF | 16 |
| AbD05322 | | |
| VH | QVQLVESGGGLVQPGGSLRLSCAASGFTFSNFWMSWVRQAPGK GLEWVSAISYSSSSTYFADSVKGRFTISRDNSKNTLYLQMNSLRAE DTAVYYCARAYRSYFDIWGQGTLVTVSS | 17 |
| H-CDR1 | GFTFSNFWMS | 18 |
| H-CDR2 | WVSAISYSSSSTYFADSVKG | 19 |
| H-CDR3 | AYRSYFDI | 20 |
| VL | DIQMTQSPSSLSASVGDRVTITCRASQSISNWLNWYQQKPGKAPKL LIYNASILQSGVPSRFSGSGSGTDFTLTISSLQPEDFAVYYCQQNYG IPITFGQGTKVEIKRT | 21 |
| L-CDR1 | RASQSISNWLN | 22 |
| L-CDR2 | LLIYNASILQS | 23 |
| L-CDR3 | QQNYGIPI | 24 |
| AbD05323 | | |
| VH | QVQLQQSGPGLVKPSQTLSLTCAISGDSVSSNSAAWGLIRQSPGR GLEWLGIIYKRSKWYNSYAVSVKSRITINPDTSKNQFSLQLNSVT PEDTAVYYCARYNYKMGLNDAANTGGFDIWGQGTLVTVSS | 25 |
| H-CDR1 | GDSVSSNSAAWG | 26 |
| H-CDR2 | WLGIIYKRSKWYNSYAVSVKS | 27 |
| H-CDR3 | YNYKMGLNDAANTGGFDI | 28 |
| VL | DIVLTQPPSVSGAPGQRVTISCSGSSSNIGSNSVKWYQQLPGTAPK LLIYSNNKRPSGVPDRFSGSKSGTSASLAITGLQSEDEADYYCGSW DTKSYVFGGGTKLTVLGQ | 29 |
| L-CDR1 | SGSSSNIGSNSVK | 30 |
| L-CDR2 | LLIYSNNKRPS | 31 |
| L-CDR3 | GSWDTKSY | 32 |
| AbD05444 | | |
| VH | QVQLVESGGGLVQPGGSLRLSCAASGFTFSSYWLNWVRQAPGKG LEWVSGISSSSSSTFYADGVKGRFTISRDNSKNTLYLQMNSLRAED TAVYYCARHSYFDYWGQGTLVTVSS | 33 |
| H-CDR1 | GFTFSSYWLN | 34 |
| H-CDR2 | WVSGISSSSSSTFYADGVKG | 35 |
| H-CDR3 | HSYFDY | 36 |
| VL | DIQMTQSPSSLSASVGDRVTITCRASQSIVTYLNWYQQKPGKAPKL LIYAASNLQSGVPSRFSGSGSGTDFTLTISSLQPEDFAVYYCQQLY SHPPTFGQGTKVEIKRT | 37 |

TABLE 2-continued

|  |  | SEQ ID NO. |
|---|---|---|
| L-CDR1 | RASQSIVTYLN | 38 |
| L-CDR2 | LLIYAASNLQS | 39 |
| L-CDR3 | QQLYSHPP | 40 |

AbD05445

| | | |
|---|---|---|
| VH | QVQLVESGGGLVQPGGSLRLSCAASGFTFSNNAMTWVRQAPGKG LEWVSLISYSGSSTYYADSVKGRFTISRDNSKNTLYLQMNSLRAED TAVYYCARLGGNPLGPFDHWGQGTLVTVSS | 41 |
| H-CDR1 | GFTFSNNAMT | 42 |
| H-CDR2 | WVSLISYSGSSTYYADSVKG | 43 |
| H-CDR3 | LGGNPLGPFDH | 44 |
| VL | DIALTQPASVSGAPGQRVTISCTGTSSDIGGYSYVSWYQQHPGKAP KLMIYGVTKRPSGVSNRFSGSKSGNTASLTISGLQAEDEADYYCQS WATHPIRVFGGGTKLTVLGQ | 45 |
| L-CDR1 | TGTSSDIGGYSYVS | 46 |
| L-CDR2 | LMIYGVTKRPS | 47 |
| L-CDR3 | QSWATHPIR | 48 |

AbD05446

| | | |
|---|---|---|
| VH | QVQLVESGGGLVQPGGSLRLSCAASGFTFNSNSMSWVRQAPGKG LEWVSGISGIGSNTNYADSVKGRFTISRDNSKNTLYLQMNSLRAED TAVYYCARVHYYSGVVFDFWGQGTLVTVSS | 49 |
| H-CDR1 | GFTFNSNSMS | 50 |
| H-CDR2 | WVSGISGIGSNTNYADSVKG | 51 |
| H-CDR3 | VHYYSGVVFDF | 52 |
| VL | DIELTQPPSVSVAPGQTARISCSGDNLRTQYASWYQQKPGQAPVL VIYNKNKRPSGIPERFSGSNSGNTATLTISGTQAEDEADYYCAAWD SGSIVFGGGTKLTVLGQ | 53 |
| L-CDR1 | SGDNLRTQYAS | 54 |
| L-CDR2 | LVIYNKNKRPS | 55 |
| L-CDR3 | AAWDSGSI | 56 |

Modified H-CDR3 of AbD05323

| | |
|---|---|
| YNYKMGRNDAANTGGFDI | 57 |
| YNYKMGLRDAANTGGFDI | 58 |
| YNYKMGLNGAANTGGFDI | 59 |
| YNYKMGRRDAANTGGFDI | 60 |
| YNYKMGLRGAANTGGFDI | 61 |
| YNYKMGRNGAANTGGFDI | 62 |
| YNYKMGRRGAANTGGFDI | 63 |
| YNYKMGLNSAANTGGFDI | 64 |
| YNYKMGLRSAANTGGFDI | 65 |
| YNYKMGRNSAANTGGFDI | 66 |
| YNYKMGRRSAANTGGFDI | 67 |
| YNYKMGLNAAANTGGFDI | 68 |
| YNYKMGLRAAANTGGFDI | 69 |
| YNYKMGRNAAANTGGFDI | 70 |
| YNYKMGRRAAANTGGFDI | 71 |

Example 3

Characterization of the Antibodies

To determine if the antibodies are resistant to NS2B-NS3pro proteolysis, the purified antibody samples (4 μg; 8 μM each) were co-incubated for 2 h at 37° C. with the purified NS2B-NS3pro K48A construct (1 μg, 1.4 μM; an enzyme-substrate molar ratio=1:6) in 10 mM Tris-HCl buffer, pH 8.0, containing 20% (v/v) glycerol and 0.005% Brij 35. The digest samples were separated by 4-20% gradient SDS-PAGE. Antibodies AbD05320, AbD05321, AbD05322 and AbD05323 antibodies were completely resistant to NS2B-NS3pro proteolysis.

To determine the inhibitory potency of the antibodies, increasing concentrations of purified AbD05320, AbD05321, AbD05322, AbD05323, AbD05444, AbD05445 and AbD05446 samples were each co-incubated for 60 min at ambient temperature with NS2B-NS3-K48A (50 nM). The residual proteolytic activity of the protease was then measured using the Pyr-RTKR-AMC fluorescent peptide substrate. A near complete inhibition of the proteolytic activity of NS2B-NS3-K48A was observed at a 300 nM concentration of AbD05320, AbD05322, AbD05323, AbD05444 and AbD05445 while AbD05321 and AbD05446 were less inhibitory. Results are depicted in FIG. 3.

Figure 4:
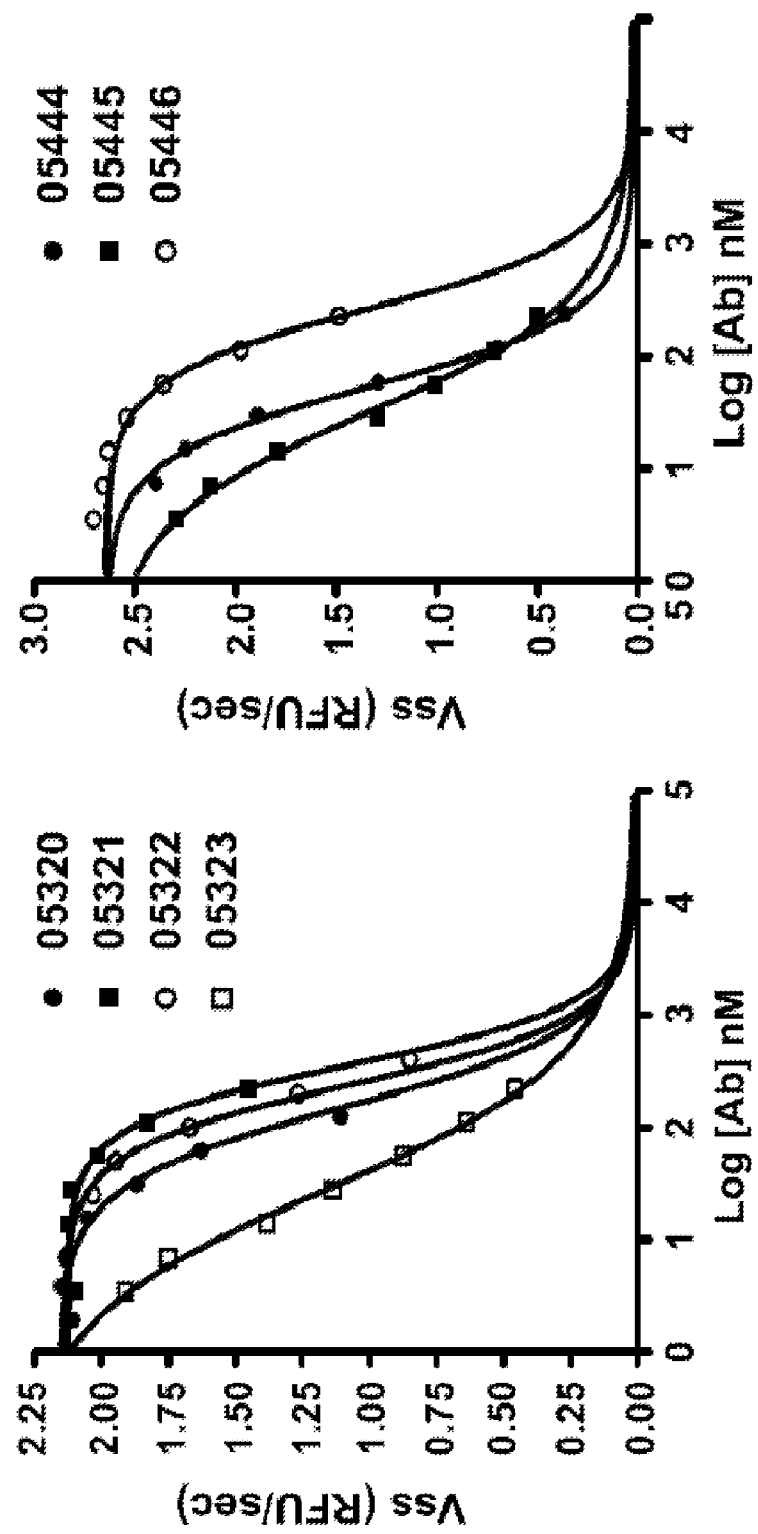

To analyze the inhibitory characteristics of the antibodies in more detail, we determined the Ki values of the antibodies. For these purposes, NS2B-NS3-K48A (10 nM) was pre-incubated with the increasing concentrations of the antibodies for 60 min at ambient temperature in 10 mM Tris-HCl buffer, pH 8.0, containing 20% (v/v) glycerol and 0.005% Brij 35. The Pyr-RTKR-AMC substrate (24 μM) was then added to the 0.1 ml reactions. We then have determined the Ki values of AbD05320, AbD05321, AbD05322, AbD05323, AbD05444, AbD05445 and AbD05446 to be 264, 400, 170, 31, 58, 35 and 288 nM, respectively. To do so, the NS2B-NS3pro constructs (50 nM) were pre-incubated with increasing concentrations of the antibodies for 30 min at ambient temperature in 0.1 ml 20 mM Tris-HCl buffer, pH 8.0, containing 20% glycerol and 0.005% Brij 35. The Pyr-RTKR-AMC substrate (25 µM) was then added in 0.1 ml of the same buffer. All assays were performed in triplicate in wells of a 96-well plate. Ki values were determined by routine kinetics software. Results are depicted in FIG. 4.

Figure 5:
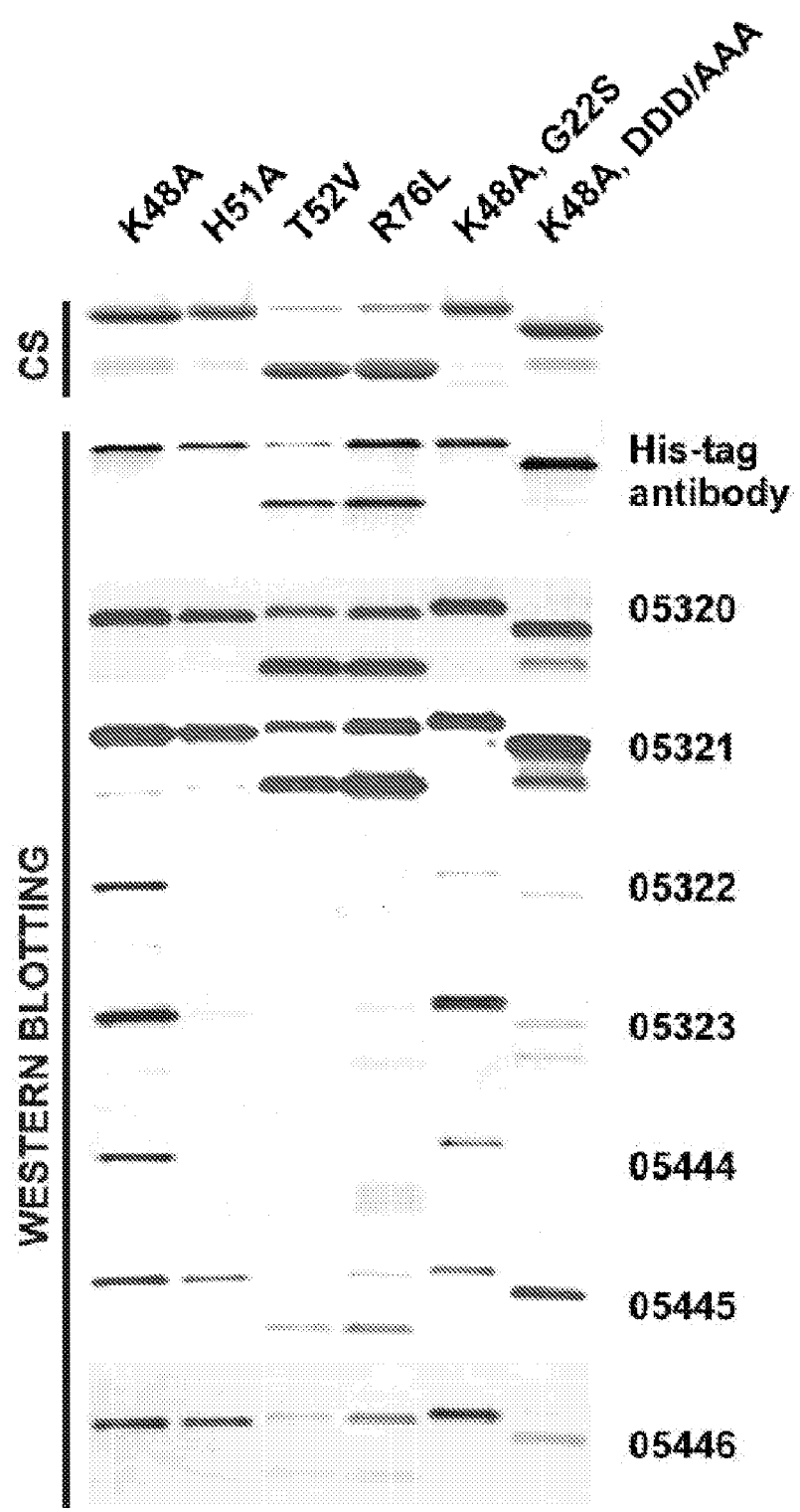

To determine if the antibodies selectively bind the NY99 and DV constructs, we used a Western blotting procedure. The purified WNV K48A, H51A, T52V, R76L, G22S and DDD/AAA constructs (100 ng each) were added to the *E. coli* soluble protein fraction (20 µg total protein) and the samples were analyzed by Western blotting with the AbD05320, AbD05321, AbD05322, AbD05323, AbD05444, AbD05445 and AbD05446 antibodies followed by a goat IgG F(ab')2 fragment conjugated with horseradish peroxidase and a TMB/M substrate. The Western Blot is shown in FIG. 5. While the G22S and DDD/AAA mutations in the NS2B cofactor did not significantly affect the binding efficiency of the antibodies, the presence of H51A, T52V and R76 mutations in the active site region of NS3pro significantly decreased the binding efficiency of the AbD05322 (Ki=170 nM), AbD05323 (Ki=31 nM) and AbD05444 (Ki=58 nM) with the WNV constructs. AbD05323 and AbD05444 were able to bind the wild-type WNV proteinase but they were totally inactive with the H51A, T52V and R76L mutants which exhibited mutations in the active site region. Four antibodies (AbD05320, AbD05321, AbD05445 and AbD05446) significantly cross-reacted with the H51 and other mutants. The $K_i$ values of the antibodies against the wild-type (WT) and mutant WNV NS2B-NS3pro are summarized in Table 3.

added to the wells and incubation was continued for 2 h at room temperature. After washing with PBS-1% BSA-0.05% Tween 20 and incubation with 0.1 ml of the TMB Super Sensitive One Component HRP Microwell Substrate solution (BioFX, Owings Mills, Md.), the reaction was stopped by the addition of 0.05 ml of 1 N HCl, and the intensity of the color reaction was measured at 450 nm using a Spectra Fluor Plus fluorescence plate reader (Tecan, Männedorf, Switzerland).

Figure 6:
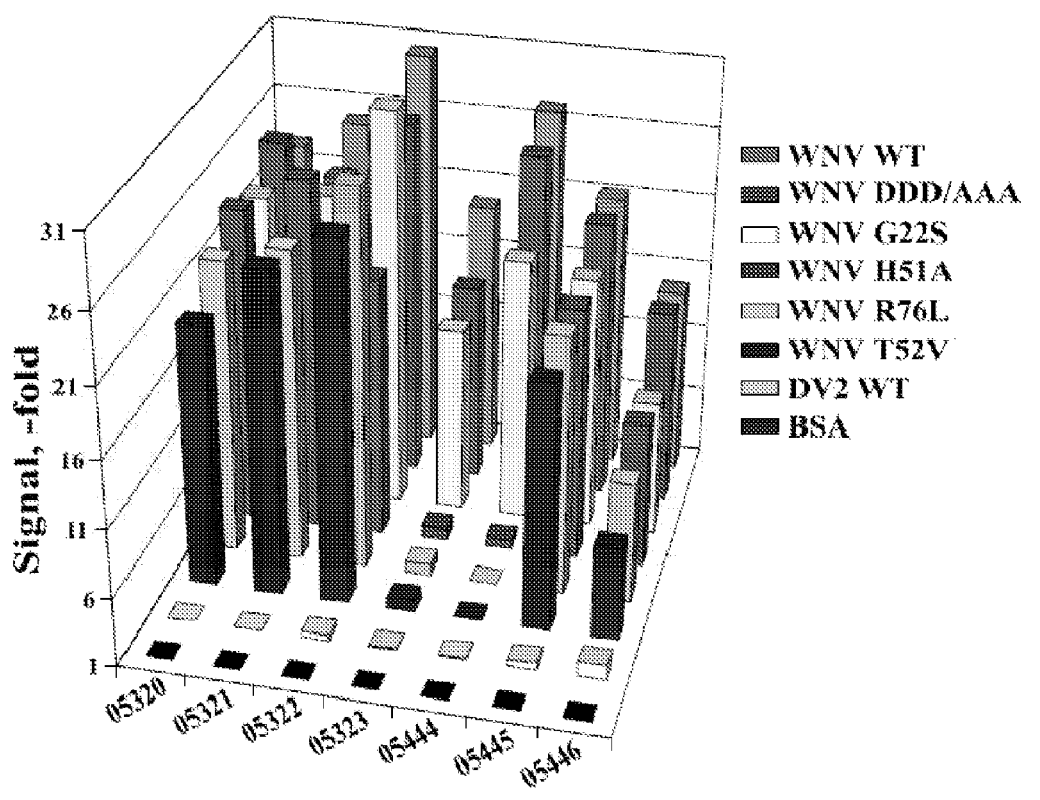

Remarkably, none of the selected anti-NY99 antibodies recognized the closely related DV proteinase. Because AbD05323 and AbD05444 did not interact with the H51A, R76L and T52V contracts, these two antibodies were clearly different when compared to the other anti-NY99 antibodies analyzed. Overall, based on our data, we concluded that the AbD05323 and AbD05444 antibodies target in a highly selective and focused manner the active site region of the two-component WNV NS2B-NS3 proteinase. Results are shown in FIG. 6.

Example 4

Optimization and Modeling Studies

Trypsin-like matriptase and flaviviral proteinases are structurally similar. Because both enzymes are serine proteinases, the level of this similarity is especially high in the active site region. Both matriptase and WNV NS2B-NS3pro require the presence of Arg at the P1' substrate position. The structure of the complex of matriptase with the inhibitory human Fab was recently solved (J Mol. Biol. 380, 351-360; J Mol. Biol. 369, 1041-1051). 2 Å resolution crystal structure of a Fab antibody inhibitor ($k_i$=15 pM) in complex with matriptase reveals the molecular basis of its picomolar potency and specificity. This anti-matriptase E2 Fab is similar to the anti-WNV AbD05323

TABLE 3

| NS2B-NS3pro | Ki [nM] | | | | | | |
|---|---|---|---|---|---|---|---|
| | AbD05320 | AbD05321 | AbD05322 | AbD05323 | AbD05444 | AbD05445 | AbD05446 |
| WT | 264 | 400 | 170 | 31 | 58 | 35 | 289 |
| T52V | 263 | 416 | 763 | 624 | 863 | 754 | 811 |
| R76L | 282 | 432 | 720 | 684 | 847 | 733 | 828 |

To corroborate these data using the native proteinase constructs (rather than partially denatured ones as in the Western blotting experiments), we performed an assessment of the antibody binding with the NY99 and DV constructs using ELISA.

Wells of a Nunc-Immuno MaxiSorp 96-well flat-bottom plate (Thermo Fisher Scientific, Rochester, N.Y.) were coated in triplicate for 18 h at 4° C. using the NY99 or DV constructs (0.1 ml/well; 1 µg/ml). Control wells were coated with 1 µg/ml BSA. After washing with PBS, unspecific binding sites were saturated by incubation with 0.2 ml 1% BSA (2 h; room temperature). The wells were then washed using PBS-0.05% Tween 20. The 2 µg/ml antibody solution (0.1 ml) in PBS-1% BSA-0.05% Tween 20 was added to the wells. After a 2 h incubation at room temperature the wells were washed using PBS-0.05% Tween 20. Goat anti-human F(ab')2 fragment conjugated with horseradish peroxidase (1:5.000 dilution in PBS-1% BSA-0.05% Tween 20 in PBS; 0.1 ml) was then Fab (79% homology) which we selected for structure optimization studies. Anti-WNV NS2B-NS3pro AbD05323 Fab, however, is a less potent inhibitor ($k_i$=30 nM). We hypothesized that using the atomic resolution structure of the trypsin-like matriptase serine proteinase with the E2 Fab antibody inhibitor and the atomic resolution structure of NS2B-NS3pro as a guide can be used to re-engineer the hypervariable loop of the AbD05323 Fab.

Because of the presence of Arg-Arg in the hypervariable loop, the E2 Fab is a 15 µM inhibitor of matriptase. Our modeling results indicate that the binding affinity of the AbD05323 Fab can be dramatically increased by replacing the original Leu-108, Asn-109 and Asp-110 sequence of the hypervariable loop with the sequence Arg-Arg-Ala/Ser/Gly. See FIG. 7. Antibodies with these mutant sequences will allow the hypervariable loop of the modified AbD05323 to enter the binding pocket of NS2B-NS3pro. This modified antibody is a particular highly potent inhibitor of this viral proteinase.

The invention claimed is:

1. A method to identify antigen-binding moieties which bind to an epitope of a polypeptide, wherein said polypeptide comprises an enzymatic activity, said method comprising (a) screening a library of antigen-binding moieties against a polypeptide comprising the epitope and having the enzymatic activity and isolating those members of said library that bind to said polypeptide, (b) counter-screening the members of the library isolated in step (a) against a variant of the polypeptide, wherein said variant polypeptide comprises a mutated epitope and is devoid of enzymatic activity, and
(c) isolating those members that do not bind to said variant polypeptide, therein identifying those members that bind to the epitope of the polypeptide.

2. The method of claim 1, wherein said variant polypeptide is an epitope mutant of the wild type polypeptide.

3. The method of claim 1, wherein said epitope of the polypeptide only exists within one or more isoforms of the polypeptide.

4. The method of claim 1, wherein said epitope of the polypeptide only exists in the monomeric, multimeric or heteromeric form of the polypeptide.

5. The method of claim 1, wherein said polypeptide is a protease.

6. The method of claim 5, wherein said protease is a viral protease.

7. The method according to claim 1, further comprising
(d) testing if the antigen-binding moieties isolated in step (c) inhibit the enzymatic activity of the polypeptide.

8. The method of claim 6, wherein said viral protease is the NS2B-NS3 protease of West Nile Virus.

9. The method of claim 1, wherein the epitope is mutated by remov

SEQUENCE LISTING

<160> NUMBER OF SEQ ID NOS: 76

<210> SEQ ID NO 1
<211> LENGTH: 117
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Ser Trp Val Arg Gln Ala Pro Gly Lys Gly Leu Glu Trp Met
        35                  40                  45

Gly Ile Ile Asp Pro Gly Asp Ser Asp Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Asn Tyr Tyr Asn Phe Asp Tyr Trp Gly Gln Gly Thr Leu
            100                 105                 110

Val Thr Val Ser Ser
        115

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Tyr Ser Phe Thr Asn Tyr Trp Ile Ser
1               5                   10

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Trp Met Gly Ile Ile Asp Pro Gly Asp Ser Asp Thr Asn Tyr Ser Pro
1               5                   10                  15

Ser Phe Gln Gly
            20

<210> SEQ ID NO 4
<211> LENGTH: 8
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 4

Val Asn Tyr Tyr Asn Phe Asp Tyr
1               5

<210> SEQ ID NO 5
<211> LENGTH: 110
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 5

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Thr Ser Asn
            20                  25                  30

Leu Ala Trp Tyr Gln Gln Lys Pro Gly Gln Ala Pro Arg Leu Leu Ile
        35                  40                  45

Tyr Gly Asn Val Ser Arg Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Gln Gln Tyr Gly Asp Tyr Pro
                85                  90                  95

Ala Thr Phe Gly Gln Gly Thr Lys Val Glu Ile Lys Arg Thr
            100                 105                 110

<210> SEQ ID NO 6
<211> LENGTH: 11
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 6

Arg Ala Ser Gln Ser Val Thr Ser Asn Leu Ala
1               5                   10

<210> SEQ ID NO 7
<211> LENGTH: 12
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 7

Leu Leu Ile Tyr Gly Asn Val Ser Arg Arg Ala Thr
1               5                   10

<210> SEQ ID NO 8
<211> LENGTH: 8
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 8

Gln Gln Tyr Gly Asp Tyr Pro Ala
1               5

```
<210> SEQ ID NO 9
<211> LENGTH: 121
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 9

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser His
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Met Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Trp Lys Pro Val Leu Phe Asp Phe Asp Val Trp Gly
            100                 105                 110

Gln Gly Thr Leu Val Thr Val Ser Ser
        115                 120

<210> SEQ ID NO 10
<211> LENGTH: 10
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 10

Gly Gly Thr Phe Ser Ser His Ala Ile Ser
1               5                   10

<210> SEQ ID NO 11
<211> LENGTH: 20
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 11

Trp Met Gly Gly Ile Ile Pro Ile Phe Gly Met Ala Asn Tyr Ala Gln
1               5                   10                  15

Lys Phe Gln Gly
            20

<210> SEQ ID NO 12
<211> LENGTH: 12
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 12

Tyr Tyr Trp Lys Pro Val Leu Phe Asp Phe Asp Val
1               5                   10
```

```
<210> SEQ ID NO 13
<211> LENGTH: 111
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 13

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Gly Asn
            20                  25                  30

Asn Tyr Val Ser Trp Tyr Gln Gln His Pro Gly Lys Ala Pro Lys Val
        35                  40                  45

Met Ile Tyr Glu Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Met Thr
                85                  90                  95

Ile Phe Val Phe Gly Gly Gly Thr Lys Leu Thr Val Leu Gly Gln
            100                 105                 110

<210> SEQ ID NO 14
<211> LENGTH: 14
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 14

Thr Gly Thr Ser Ser Asp Ile Gly Gly Asn Asn Tyr Val Ser
1               5                   10

<210> SEQ ID NO 15
<211> LENGTH: 11
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 15

Val Met Ile Tyr Glu Val Ser Lys Arg Pro Ser
1               5                   10

<210> SEQ ID NO 16
<211> LENGTH: 8
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 16

Ser Ser Tyr Thr Met Thr Ile Phe
1               5

<210> SEQ ID NO 17
<211> LENGTH: 117
<212> TYPE: PRT
<213> ORGANISM: Artificial Sequence
```

```
<220> FEATURE:
<223> OTHER INFORMATION: /note="Description of Artificial Sequence:
      Synthetic peptide"

<400> SEQUENCE: 17

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
            20                  25                  30

Trp Met Ser Trp Val Arg Gln Ala Pro Gly Lys Gly Leu Glu Trp Val
        35                  40                  45

Ser Ala Ile Ser Tyr Ser Ser Ser Thr Tyr Phe Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Tyr Arg Ser Tyr Phe Asp Ile Trp Gly Gln Gly Thr Leu
            100                 105                 110

Val Thr Val Ser Ser
        115

<210> SEQ ID NO 18
<211> LENGTH: 10
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 18

Gly Phe Thr Phe Ser Asn Phe Trp Met Ser
1               5                   10

<210> SEQ ID NO 19
<211> LENGTH: 20
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 19

Trp Val Ser Ala Ile Ser Tyr Ser Ser Ser Thr Tyr Phe Ala Asp
1               5                   10                  15

Ser Val Lys Gly
        20

<210> SEQ ID NO 20
<211> LENGTH: 8
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 20

Ala Tyr Arg Ser Tyr Phe Asp Ile
1               5
```

```
<210> SEQ ID NO 21
<211> LENGTH: 109
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Trp
            20                  25                  30

Leu Asn Trp Tyr Gln Gln Lys Pro Gly Lys Ala Pro Lys Leu Leu Ile
        35                  40                  45

Tyr Asn Ala Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Asn Tyr Gly Ile Pro Ile
                85                  90                  95

Thr Phe Gly Gln Gly Thr Lys Val Glu Ile Lys Arg Thr
            100                 105

<210> SEQ ID NO 22
<211> LENGTH: 11
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 22

Arg Ala Ser Gln Ser Ile Ser Asn Trp Leu Asn
1               5                   10

<210> SEQ ID NO 23
<211> LENGTH: 11
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 23

Leu Leu Ile Tyr Asn Ala Ser Ile Leu Gln Ser
1               5                   10

<210> SEQ ID NO 24
<211> LENGTH: 8
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 24

Gln Gln Asn Tyr Gly Ile Pro Ile
1               5

<210> SEQ ID NO 25
<211> LENGTH: 130
<212> TYPE: PRT
<213> ORGANISM: Artificial Sequence
```

<220> FEATURE:
<223> OTHER INFORMATION: /note="Description of Artificial Sequence: Synthetic peptide"

<400> SEQUENCE: 25

```
Gln Val Gln Leu Gln Gln Ser Gly Pro Gly Leu Val Lys Pro Ser Gln
1               5                   10                  15
Thr Leu Ser Leu Thr Cys Ala Ile Ser Gly Asp Ser Val Ser Ser Asn
            20                  25                  30
Ser Ala Ala Trp Gly Leu Ile Arg Gln Ser Pro Gly Arg Gly Leu Glu
        35                  40                  45
Trp Leu Gly Ile Ile Tyr Lys Arg Ser Lys Trp Tyr Asn Ser Tyr Ala
    50                  55                  60
Val Ser Val Lys Ser Arg Ile Thr Ile Asn Pro Asp Thr Ser Lys Asn
65                  70                  75                  80
Gln Phe Ser Leu Gln Leu Asn Ser Val Thr Pro Glu Asp Thr Ala Val
                85                  90                  95
Tyr Tyr Cys Ala Arg Tyr Asn Tyr Lys Met Gly Leu Asn Asp Ala Ala
            100                 105                 110
Asn Thr Gly Gly Phe Asp Ile Trp Gly Gln Gly Thr Leu Val Thr Val
        115                 120                 125
Ser Ser
    130
```

<210> SEQ ID NO 26
<211> LENGTH: 12
<212> TYPE: PRT
<213> ORGANISM: Artificial Sequence
<220> FEATURE:
<223> OTHER INFORMATION: /note="Description of Artificial Sequence: Synthetic peptide"

<400> SEQUENCE: 26

```
Gly Asp Ser Val Ser Ser Asn Ser Ala Ala Trp Gly
1               5                   10
```

<210> SEQ ID NO 27
<211> LENGTH: 21
<212> TYPE: PRT
<213> ORGANISM: Artificial Sequence
<220> FEATURE:
<223> OTHER INFORMATION: /note="Description of Artificial Sequence: Synthetic peptide"

<400> SEQUENCE: 27

```
Trp Leu Gly Ile Ile Tyr Lys Arg Ser Lys Trp Tyr Asn Ser Tyr Ala
1               5                   10                  15
Val Ser Val Lys Ser
            20
```

<210> SEQ ID NO 28
<211> LENGTH: 18
<212> TYPE: PRT
<213> ORGANISM: Artificial Sequence
<220> FEATURE:
<223> OTHER INFORMATION: /note="Description of Artificial Sequence: Synthetic peptide"

<400> SEQUENCE: 28

```
Tyr Asn Tyr Lys Met Gly Leu Asn Asp Ala Ala Asn Thr Gly Gly Phe
1               5                   10                  15
Asp Ile
```

```
<210> SEQ ID NO 29
<211> LENGTH: 110
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 29

Asp Ile Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Ser Asn
            20                  25                  30

Ser Val Lys Trp Tyr Gln Gln Leu Pro Gly Thr Ala Pro Lys Leu Leu
        35                  40                  45

Ile Tyr Ser Asn Asn Lys Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gly Ser Trp Asp Thr Lys Ser
                85                  90                  95

Tyr Val Phe Gly Gly Gly Thr Lys Leu Thr Val Leu Gly Gln
            100                 105                 110

<210> SEQ ID NO 30
<211> LENGTH: 13
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 30

Ser Gly Ser Ser Ser Asn Ile Gly Ser Asn Ser Val Lys
1               5                   10

<210> SEQ ID NO 31
<211> LENGTH: 11
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 31

Leu Leu Ile Tyr Ser Asn Asn Lys Arg Pro Ser
1               5                   10

<210> SEQ ID NO 32
<211> LENGTH: 8
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 32

Gly Ser Trp Asp Thr Lys Ser Tyr
1               5

<210> SEQ ID NO 33
<211> LENGTH: 115
<212> TYPE: PRT
<213> ORGANISM: Artificial Sequence
```

-continued

<220> FEATURE:
<223> OTHER INFORMATION: /note="Description of Artificial Sequence: Synthetic peptide"

<400> SEQUENCE: 33

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Leu Asn Trp Val Arg Gln Ala Pro Gly Lys Gly Leu Glu Trp Val
        35                  40                  45

Ser Gly Ile Ser Ser Ser Ser Ser Thr Phe Tyr Ala Asp Gly Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ser Tyr Phe Asp Tyr Trp Gly Gln Gly Thr Leu Val Thr
            100                 105                 110

Val Ser Ser
        115

<210> SEQ ID NO 34
<211> LENGTH: 10
<212> TYPE: PRT
<213> ORGANISM: Artificial Sequence
<220> FEATURE:
<223> OTHER INFORMATION: /note="Description of Artificial Sequence: Synthetic peptide"

<400> SEQUENCE: 34

Gly Phe Thr Phe Ser Ser Tyr Trp Leu Asn
1               5                   10

<210> SEQ ID NO 35
<211> LENGTH: 20
<212> TYPE: PRT
<213> ORGANISM: Artificial Sequence
<220> FEATURE:
<223> OTHER INFORMATION: /note="Description of Artificial Sequence: Synthetic peptide"

<400> SEQUENCE: 35

Trp Val Ser Gly Ile Ser Ser Ser Ser Ser Thr Phe Tyr Ala Asp
1               5                   10                  15

Gly Val Lys Gly
            20

<210> SEQ ID NO 36
<211> LENGTH: 6
<212> TYPE: PRT
<213> ORGANISM: Artificial Sequence
<220> FEATURE:
<223> OTHER INFORMATION: /note="Description of Artificial Sequence: Synthetic peptide"

<400> SEQUENCE: 36

His Ser Tyr Phe Asp Tyr
1               5

```
<210> SEQ ID NO 37
<211> LENGTH: 109
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Val Thr Tyr
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Leu Tyr Ser His Pro Pro
                85                  90                  95

Thr Phe Gly Gln Gly Thr Lys Val Glu Ile Lys Arg Thr
            100                 105

<210> SEQ ID NO 38
<211> LENGTH: 11
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 38

Arg Ala Ser Gln Ser Ile Val Thr Tyr Leu Asn
1               5                   10

<210> SEQ ID NO 39
<211> LENGTH: 11
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 39

Leu Leu Ile Tyr Ala Ala Ser Asn Leu Gln Ser
1               5                   10

<210> SEQ ID NO 40
<211> LENGTH: 8
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 40

Gln Gln Leu Tyr Ser His Pro Pro
1               5

<210> SEQ ID NO 41
<211> LENGTH: 120
<212> TYPE: PRT
<213> ORGANISM: Artificial Sequence
```

<220> FEATURE:
<223> OTHER INFORMATION: /note="Description of Artificial Sequence:
      Synthetic peptide"

<400> SEQUENCE: 41

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Asn
            20                  25                  30

Ala Met Thr Trp Val Arg Gln Ala Pro Gly Lys Gly Leu Glu Trp Val
        35                  40                  45

Ser Leu Ile Ser Tyr Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Gly Asn Pro Leu Gly Pro Phe Asp His Trp Gly Gln
            100                 105                 110

Gly Thr Leu Val Thr Val Ser Ser
        115                 120

<210> SEQ ID NO 42
<211> LENGTH: 10
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 42

Gly Phe Thr Phe Ser Asn Asn Ala Met Thr
1               5                   10

<210> SEQ ID NO 43
<211> LENGTH: 20
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 43

Trp Val Ser Leu Ile Ser Tyr Ser Gly Ser Ser Thr Tyr Tyr Ala Asp
1               5                   10                  15

Ser Val Lys Gly
            20

<210> SEQ ID NO 44
<211> LENGTH: 11
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 44

Leu Gly Gly Asn Pro Leu Gly Pro Phe Asp His
1               5                   10

```
<210> SEQ ID NO 45
<211> LENGTH: 112
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 45

Asp Ile Ala Leu Thr Gln Pro Ala Ser Val Ser Gly Ala Pro Gly Gln
1               5                   10                  15

Arg Val Thr Ile Ser Cys Thr Gly Thr Ser Ser Asp Ile Gly Gly Tyr
            20                  25                  30

Ser Tyr Val Ser Trp Tyr Gln Gln His Pro Gly Lys Ala Pro Lys Leu
        35                  40                  45

Met Ile Tyr Gly Val Thr Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Trp Ala Thr His
                85                  90                  95

Pro Ile Arg Val Phe Gly Gly Gly Thr Lys Leu Thr Val Leu Gly Gln
            100                 105                 110

<210> SEQ ID NO 46
<211> LENGTH: 14
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 46

Thr Gly Thr Ser Ser Asp Ile Gly Gly Tyr Ser Tyr Val Ser
1               5                   10

<210> SEQ ID NO 47
<211> LENGTH: 11
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 47

Leu Met Ile Tyr Gly Val Thr Lys Arg Pro Ser
1               5                   10

<210> SEQ ID NO 48
<211> LENGTH: 9
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 48

Gln Ser Trp Ala Thr His Pro Ile Arg
1               5

<210> SEQ ID NO 49
<211> LENGTH: 120
<212> TYPE: PRT
<213> ORGANISM: Artificial Sequence
```

```
<220> FEATURE:
<223> OTHER INFORMATION: /note="Description of Artificial Sequence:
      Synthetic peptide"

<400> SEQUENCE: 49

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Ser Asn
            20                  25                  30

Ser Met Ser Trp Val Arg Gln Ala Pro Gly Lys Gly Leu Glu Trp Val
        35                  40                  45

Ser Gly Ile Ser Gly Ile Gly Ser Asn Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val His Tyr Tyr Ser Gly Val Val Phe Asp Phe Trp Gly Gln
            100                 105                 110

Gly Thr Leu Val Thr Val Ser Ser
        115                 120

<210> SEQ ID NO 50
<211> LENGTH: 10
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 50

Gly Phe Thr Phe Asn Ser Asn Ser Met Ser
1               5                   10

<210> SEQ ID NO 51
<211> LENGTH: 20
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 51

Trp Val Ser Gly Ile Ser Gly Ile Gly Ser Asn Thr Asn Tyr Ala Asp
1               5                   10                  15

Ser Val Lys Gly
            20

<210> SEQ ID NO 52
<211> LENGTH: 11
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 52

Val His Tyr Tyr Ser Gly Val Val Phe Asp Phe
1               5                   10
```

-continued

```
<210> SEQ ID NO 53
<211> LENGTH: 108
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 53

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Arg Thr Gln Tyr Ala
            20                  25                  30

Ser Trp Tyr Gln Gln Lys Pro Gly Gln Ala Pro Val Leu Val Ile Tyr
        35                  40                  45

Asn Lys Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ala Ala Trp Asp Ser Gly Ile Val
                85                  90                  95

Phe Gly Gly Gly Thr Lys Leu Thr Val Leu Gly Gln
            100                 105

<210> SEQ ID NO 54
<211> LENGTH: 11
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 54

Ser Gly Asp Asn Leu Arg Thr Gln Tyr Ala Ser
1               5                   10

<210> SEQ ID NO 55
<211> LENGTH: 11
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 55

Leu Val Ile Tyr Asn Lys Asn Lys Arg Pro Ser
1               5                   10

<210> SEQ ID NO 56
<211> LENGTH: 8
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 56

Ala Ala Trp Asp Ser Gly Ser Ile
1               5

<210> SEQ ID NO 57
<211> LENGTH: 18
<212> TYPE: PRT
<213> ORGANISM: Artificial Sequence
```

```
<220> FEATURE:
<223> OTHER INFORMATION: /note="Description of Artificial Sequence:
      Synthetic peptide"

<400> SEQUENCE: 57

Tyr Asn Tyr Lys Met Gly Arg Asn Asp Ala Ala Asn Thr Gly Gly Phe
1               5                   10                  15

Asp Ile

<210> SEQ ID NO 58
<211> LENGTH: 18
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 58

Tyr Asn Tyr Lys Met Gly Leu Arg Asp Ala Ala Asn Thr Gly Gly Phe
1               5                   10                  15

Asp Ile

<210> SEQ ID NO 59
<211> LENGTH: 18
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 59

Tyr Asn Tyr Lys Met Gly Leu Asn Gly Ala Ala Asn Thr Gly Gly Phe
1               5                   10                  15

Asp Ile

<210> SEQ ID NO 60
<211> LENGTH: 18
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 60

Tyr Asn Tyr Lys Met Gly Arg Arg Asp Ala Ala Asn Thr Gly Gly Phe
1               5                   10                  15

Asp Ile

<210> SEQ ID NO 61
<211> LENGTH: 18
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 61

Tyr Asn Tyr Lys Met Gly Leu Arg Gly Ala Ala Asn Thr Gly Gly Phe
1               5                   10                  15

Asp Ile
```

```
<210> SEQ ID NO 62
<211> LENGTH: 18
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 62

Tyr Asn Tyr Lys Met Gly Arg Asn Gly Ala Ala Asn Thr Gly Gly Phe
1               5                   10                  15

Asp Ile

<210> SEQ ID NO 63
<211> LENGTH: 18
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 63

Tyr Asn Tyr Lys Met Gly Arg Arg Gly Ala Ala Asn Thr Gly Gly Phe
1               5                   10                  15

Asp Ile

<210> SEQ ID NO 64
<211> LENGTH: 18
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 64

Tyr Asn Tyr Lys Met Gly Leu Asn Ser Ala Ala Asn Thr Gly Gly Phe
1               5                   10                  15

Asp Ile

<210> SEQ ID NO 65
<211> LENGTH: 18
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 65

Tyr Asn Tyr Lys Met Gly Leu Arg Ser Ala Ala Asn Thr Gly Gly Phe
1               5                   10                  15

Asp Ile

<210> SEQ ID NO 66
<211> LENGTH: 18
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 66

Tyr Asn Tyr Lys Met Gly Arg Asn Ser Ala Ala Asn Thr Gly Gly Phe
1               5                   10                  15

Asp Ile
```

```
<210> SEQ ID NO 67
<211> LENGTH: 18
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 67

Tyr Asn Tyr Lys Met Gly Arg Arg Ser Ala Ala Asn Thr Gly Gly Phe
1               5                   10                  15

Asp Ile

<210> SEQ ID NO 68
<211> LENGTH: 18
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 68

Tyr Asn Tyr Lys Met Gly Leu Asn Ala Ala Ala Asn Thr Gly Gly Phe
1               5                   10                  15

Asp Ile

<210> SEQ ID NO 69
<211> LENGTH: 18
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 69

Tyr Asn Tyr Lys Met Gly Leu Arg Ala Ala Ala Asn Thr Gly Gly Phe
1               5                   10                  15

Asp Ile

<210> SEQ ID NO 70
<211> LENGTH: 18
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 70

Tyr Asn Tyr Lys Met Gly Arg Asn Ala Ala Ala Asn Thr Gly Gly Phe
1               5                   10                  15

Asp Ile

<210> SEQ ID NO 71
<211> LENGTH: 18
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 71

Tyr Asn Tyr Lys Met Gly Arg Arg Ala Ala Ala Asn Thr Gly Gly Phe
1               5                   10                  15

Asp Ile
```

-continued

```
<210> SEQ ID NO 72
<211> LENGTH: 242
<212> TYPE: PRT
<213> ORGANISM: West Nile Virus

<400> SEQUENCE: 72

Ser Thr Asp Met Trp Ile Glu Arg Thr Ala Asp Ile Thr Trp Glu Ser
1               5                   10                  15

Asp Ala Glu Ile Thr Gly Ser Ser Glu Arg Val Asp Val Arg Leu Asp
                20                  25                  30

Asp Asp Gly Asn Phe Gln Leu Met Asn Asp Pro Gly Ala Pro Trp Lys
            35                  40                  45

Gly Gly Gly Gly Ser Gly Gly Gly Gly Val Leu Trp Asp Thr
        50                  55                  60

Pro Ser Pro Lys Glu Tyr Lys Lys Gly Asp Thr Thr Thr Gly Val Tyr
65                  70                  75                  80

Arg Ile Met Thr Arg Gly Leu Leu Gly Ser Tyr Gln Ala Gly Ala Gly
                85                  90                  95

Val Met Val Glu Gly Val Phe His Thr Leu Trp His Thr Thr Lys Gly
                100                 105                 110

Ala Ala Leu Met Ser Gly Glu Gly Arg Leu Asp Pro Tyr Trp Gly Ser
            115                 120                 125

Val Lys Glu Asp Arg Leu Cys Tyr Gly Gly Pro Trp Lys Leu Gln His
        130                 135                 140

Lys Trp Asn Gly His Asp Glu Val Gln Met Ile Val Val Glu Pro Gly
145                 150                 155                 160

Lys Asn Val Lys Asn Val Gln Thr Lys Pro Gly Val Phe Lys Thr Pro
                165                 170                 175

Glu Gly Glu Ile Gly Ala Val Thr Leu Asp Tyr Pro Thr Gly Thr Ser
                180                 185                 190

Gly Ser Pro Ile Val Asp Lys Asn Gly Asp Val Ile Gly Leu Tyr Gly
            195                 200                 205

Asn Gly Val Ile Met Pro Asn Gly Ser Tyr Ile Ser Ala Ile Val Gln
        210                 215                 220

Gly Glu Arg Met Glu Glu Pro Ala Pro Ala Gly Phe His His His His
225                 230                 235                 240

His His

<210> SEQ ID NO 73
<211> LENGTH: 242
<212> TYPE: PRT
<213> ORGANISM: Dengue Virus

<400> SEQUENCE: 73

Ser Ala Asp Leu Glu Leu Glu Arg Ala Ala Asp Val Lys Trp Glu Asp
1               5                   10                  15

Gln Ala Glu Ile Ser Gly Ser Ser Pro Ile Leu Ser Ile Thr Ile Ser
                20                  25                  30

Glu Asp Gly Ser Met Ser Ile Lys Asn Glu Glu Glu Gln Thr Leu
            35                  40                  45

Gly Gly Gly Gly Ser Gly Gly Gly Gly Ala Gly Val Leu Trp Asp Val
        50                  55                  60

Pro Ser Pro Pro Pro Val Gly Lys Ala Glu Leu Glu Asp Gly Ala Tyr
65                  70                  75                  80

Arg Ile Lys Gln Lys Gly Ile Leu Gly Tyr Ser Gln Ile Gly Ala Gly
                85                  90                  95
```

```
Val Tyr Lys Glu Gly Thr Phe His Thr Met Trp His Val Thr Arg Gly
            100                 105                 110

Ala Val Leu Met His Lys Gly Lys Arg Ile Glu Pro Ser Trp Ala Asp
            115                 120                 125

Val Lys Lys Asp Leu Ile Ser Tyr Gly Gly Trp Lys Leu Glu Gly
        130                 135                 140

Glu Trp Lys Glu Gly Glu Val Gln Val Leu Ala Leu Glu Pro Gly
145                 150                 155                 160

Lys Asn Pro Arg Ala Val Gln Thr Lys Pro Gly Leu Phe Lys Thr Asn
                165                 170                 175

Ala Gly Thr Ile Gly Ala Val Ser Leu Asp Phe Ser Pro Gly Thr Ser
            180                 185                 190

Gly Ser Pro Ile Ile Asp Lys Lys Gly Lys Val Val Gly Leu Tyr Gly
            195                 200                 205

Asn Gly Val Val Thr Arg Ser Gly Ala Tyr Val Ser Ala Ile Ala Gln
            210                 215                 220

Thr Glu Lys Ser Ile Glu Asp Asn Pro Glu Ile Glu His His His His
225                 230                 235                 240

His His

<210> SEQ ID NO 74
<211> LENGTH: 19
<212> TYPE: PRT
<213> ORGANISM: Artificial Sequence
<220> FEATURE:
<223> OTHER INFORMATION: Synthetic peptide

<400> SEQUENCE: 74

Cys Ala Arg Pro Tyr Leu Thr Tyr Pro Gln Arg Arg Gln Pro Gln Asn
1               5                   10                  15

Val Ser Pro

<210> SEQ ID NO 75
<211> LENGTH: 18
<212> TYPE: PRT
<213> ORGANISM: Artificial Sequence
<220> FEATURE:
<223> OTHER INFORMATION: Synthetic peptide

<400> SEQUENCE: 75

Cys Ala Arg Tyr Asn Tyr Lys Met Gly Leu Asn Asp Ala Ala Asn Thr
1               5                   10                  15

Gly Gly

<210> SEQ ID NO 76
<211> LENGTH: 18
<212> TYPE: PRT
<213> ORGANISM: Artificial Sequence
<220> FEATURE:
<223> OTHER INFORMATION: Synthetic peptide

<400> SEQUENCE: 76

Cys Ala Arg Tyr Asn Tyr Lys Met Gly Arg Arg Gly Ala Ala Asn Thr
1               5                   10                  15

Gly Gly
```